(12) United States Patent
Ly et al.

(10) Patent No.: US 9,637,460 B2
(45) Date of Patent: *May 2, 2017

(54) ISOTOPICALLY ENRICHED ARYLSULFONAMIDE CCR3 ANTAGONISTS

(71) Applicant: Axikin Pharmaceuticals, Inc., San Diego, CA (US)

(72) Inventors: Tai Wei Ly, San Diego, CA (US); Garrett Thomas Potter, Redlands, CA (US)

(73) Assignee: Axikin Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/798,356

(22) Filed: Jul. 13, 2015

(65) Prior Publication Data

US 2015/0315158 A1 Nov. 5, 2015

Related U.S. Application Data

(63) Continuation of application No. 14/020,597, filed on Sep. 6, 2013.

(60) Provisional application No. 61/698,390, filed on Sep. 7, 2012.

(51) Int. Cl.
| | | |
|---|---|---|
| *C07D 241/08* | (2006.01) | |
| *A61K 45/06* | (2006.01) | |
| *A61K 31/495* | (2006.01) | |
| *C07B 59/00* | (2006.01) | |

(52) U.S. Cl.
CPC .......... *C07D 241/08* (2013.01); *A61K 31/495* (2013.01); *A61K 45/06* (2013.01); *C07B 59/002* (2013.01)

(58) Field of Classification Search
CPC .... C07D 241/08; C07B 59/002; A61K 45/06; A61K 31/495
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,328,245 A | 5/1982 | Yu et al. | |
| 4,409,239 A | 10/1983 | Yu | |
| 4,410,545 A | 10/1983 | Yu et al. | |
| 5,033,252 A | 7/1991 | Carter | |
| 5,052,558 A | 10/1991 | Carter | |
| 5,059,595 A | 10/1991 | Le Grazie | |
| 5,073,543 A | 12/1991 | Marshall et al. | |
| 5,120,548 A | 6/1992 | McClelland et al. | |
| 5,323,907 A | 6/1994 | Kalvelage | |
| 5,354,556 A | 10/1994 | Sparks et al. | |
| 5,591,767 A | 1/1997 | Mohr et al. | |
| 5,612,059 A | 3/1997 | Cardinal et al. | |
| 5,639,476 A | 6/1997 | Oshlack et al. | |
| 5,639,480 A | 6/1997 | Bodmer et al. | |
| 5,674,533 A | 10/1997 | Santus et al. | |
| 5,698,220 A | 12/1997 | Cardinal et al. | |
| 5,709,874 A | 1/1998 | Hanson et al. | |
| 5,733,566 A | 3/1998 | Lewis | |
| 5,739,108 A | 4/1998 | Mitchell | |
| 5,759,542 A | 6/1998 | Gurewich | |
| 5,798,119 A | 8/1998 | Herbig et al. | |
| 5,840,674 A | 11/1998 | Yatvin et al. | |
| 5,891,474 A | 4/1999 | Busetti et al. | |
| 5,900,252 A | 5/1999 | Calanchi et al. | |

(Continued)

FOREIGN PATENT DOCUMENTS

| | | |
|---|---|---|
| JP | 2003/081937 A | 3/2003 |
| WO | 02/17918 A2 | 3/2002 |

(Continued)

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modern Pharmaceutics, Marcel Dekker, New York, 1996.*
West, Anthony R., Solid State Chemistry and Its Applications, Wiley, New York, 1988, 358.*
Dyck, Journal of Neurochemistry vol. 46 Issue 2, pp. 399-404 (1986).*
Tonn, Biological Mass Spectrometry vol. 22 Issue 11, pp. 633-642 (1993).*
Haskins, Biomedical Spectrometry vol. 9 Issue 7, pp. 269-277 (1982).*
Wolen, J. of Clinical Pharmacology 1986; 26: 419-424.*

(Continued)

*Primary Examiner* — Erich Leeser
(74) *Attorney, Agent, or Firm* — Jones Day

(57) ABSTRACT

Provided herein are isotopically enriched arylsulfonamides, for example, of Formula I, that are useful for modulating CCR3 activity, and pharmaceutical compositions thereof. Also provided herein are methods of their use for treating, preventing, or ameliorating one or more symptoms of a CCR3-mediated disease, disorder, or condition.

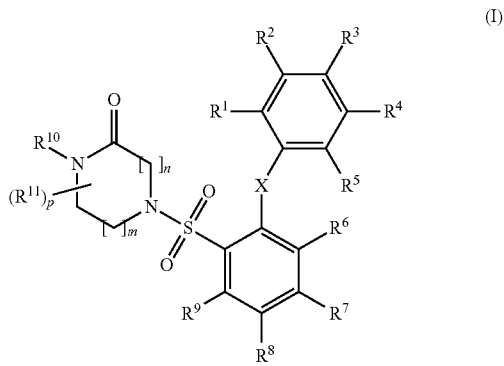

(I)

47 Claims, No Drawings

(56) References Cited

U.S. PATENT DOCUMENTS

| | | | |
|---|---|---|---|
| 5,922,356 | A | 7/1999 | Koseki et al. |
| 5,972,366 | A | 10/1999 | Haynes et al. |
| 5,972,891 | A | 10/1999 | Kamei et al. |
| 5,980,945 | A | 11/1999 | Ruiz |
| 5,985,307 | A | 11/1999 | Hanson et al. |
| 5,993,855 | A | 11/1999 | Yoshimoto et al. |
| 6,004,534 | A | 12/1999 | Langer et al. |
| 6,039,975 | A | 3/2000 | Shah et al. |
| 6,045,830 | A | 4/2000 | Igari et al. |
| 6,048,736 | A | 4/2000 | Kosak |
| 6,060,082 | A | 5/2000 | Chen et al. |
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,197,350 | B1 | 3/2001 | Yamagata et al. |
| 6,221,335 | B1 * | 4/2001 | Foster .................. C07B 59/002 424/1.81 |
| 6,248,363 | B1 | 6/2001 | Patel et al. |
| 6,253,872 | B1 | 7/2001 | Neumann |
| 6,264,970 | B1 | 7/2001 | Hata et al. |
| 6,267,981 | B1 | 7/2001 | Okamoto et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,350,458 | B1 | 2/2002 | Modi |
| 6,376,461 | B1 | 4/2002 | Igari et al. |
| 6,419,961 | B1 | 7/2002 | Igari et al. |
| 6,440,710 | B1 * | 8/2002 | Keinan .................. C12P 13/02 435/147 |
| 6,589,548 | B1 | 7/2003 | Oh et al. |
| 6,603,008 | B1 * | 8/2003 | Ando .................. C07D 405/14 546/269.7 |
| 6,613,358 | B2 | 9/2003 | Randolph et al. |
| 6,699,500 | B2 | 3/2004 | Okada et al. |
| 6,974,869 | B2 | 12/2005 | DeLucca |
| 7,517,990 | B2 * | 4/2009 | Ito ...................... C07B 59/002 546/184 |
| 7,674,797 | B2 | 3/2010 | Li et al. |
| 7,700,586 | B2 | 4/2010 | Li et al. |
| 7,759,339 | B2 | 7/2010 | Aertgeerts et al. |
| 8,318,747 | B2 | 11/2012 | Ly et al. |
| 8,399,456 | B2 | 3/2013 | Ly et al. |
| 8,420,639 | B2 | 4/2013 | Ly et al. |
| 8,741,894 | B2 | 6/2014 | Ly et al. |
| 8,999,995 | B2 * | 4/2015 | Ly .................... C07D 295/26 514/255.02 |
| 9,156,799 | B2 * | 10/2015 | Ly .................... A61K 31/495 |
| 2005/0070582 | A1 | 3/2005 | Li et al. |
| 2006/0122197 | A1 | 6/2006 | Yao et al. |
| 2007/0082929 | A1 * | 4/2007 | Gant .................. C07D 401/12 514/338 |
| 2007/0197695 | A1 * | 8/2007 | Potyen .................. C08K 5/55 524/110 |
| 2009/0286771 | A1 | 11/2009 | Li et al. |
| 2010/0273782 | A1 | 10/2010 | Ly et al. |
| 2010/0273785 | A1 | 10/2010 | Ly et al. |
| 2010/0273795 | A1 | 10/2010 | Ly et al. |
| 2011/0218207 | A1 | 9/2011 | Ly et al. |
| 2012/0088769 | A1 | 4/2012 | Ly |

FOREIGN PATENT DOCUMENTS

| | | | |
|---|---|---|---|
| WO | 03/022277 | A1 | 3/2003 |
| WO | 2004/084898 | A1 | 10/2004 |
| WO | 2006/020598 | A2 | 2/2006 |
| WO | 2008/063600 | A2 | 5/2008 |
| WO | 2010/123956 | A2 | 10/2010 |
| WO | 2010/123959 | A2 | 10/2010 |
| WO | WO 2010123959 | * 10/2010 | ............ C07D 211/96 |
| WO | 2010/123956 | A3 | 9/2011 |
| WO | 2011/109345 | A1 | 9/2011 |

OTHER PUBLICATIONS

Browne, J. of Clinical Pharmacology, 1998; 38: 213-220.*
Baillie, Pharmacology Rev.1981; 33: 81-132.*
Gouyette, Biomedical and Environmental Mass Spectrometry, vol. 15, 243-247 (1988).*
Cherrah, Biomedical and Environmental Mass Spectrometry vol. 14 Issue 11, pp. 653-657 (1987).*
Pieniaszek, J Clin Pharmacol.1999; 39: 817-825.*
Honma et al., Drug Metab. Dispos. 15 (4): 551 (1987).*
Verma et al., "Osmotically controlled oral drug delivery," Drug Development and Industrial Pharmacy, 26(7):695-708 (2000).
Waller et al., "Prodrugs," Br. J. Clin. Pharmacol. 28(5):497-507 (1989).
Wang et al., "Prodrug approaches to the improved delivery of peptide drugs," Curr. Pharm. Design 5(4):265-287 (1999).
Wermuth et al., "Designing prodrugs and bioprecursors ," The Practice of Medicinal Chemistry, Academic Press Inc., San Diego, CA, pp. 671-696 (1996).
Wiebe and Knaus, "Concepts for the design of anti-HIV nucleoside prodrugs for treating cephalic HIV infection," Adv. Drug Delivery Rev. 39(1-3):63-80 (1999).
Wolen, "The application of stable isotopes to studies of drug bioavailability and bioequivalence," J. Clin. Pharmacol. 26(6):419-424 (1986).
Wolf, Manfred E., Burger's Medicinal Chemistry and Drug Discovery, Fifth Ed., vol. 1: Principles and Practice, John Wiley & Sons, 1995, 975.
Ying et al., "Eosinophil chemotactic chemokines (eotaxin, eotaxin-2, RANTES, monocyte chemoattractant protein-3 (MCP-3), and MCP-4), and C-C chemokine receptor 3 expression in bronchial biopsies from atopic and nonatopic (Intrinsic) asthmatics," J. Immunol. 163(11):6321-6329 (1999).
Byrn et al., Solid-State Chemistry of Drugs, 2nd ed. 1999, pp. 233-247.
Foster, A.B., "Deuterium isotope effects in the metabolism of drugs and xenobiotics: implications for drug design," Adv. Drug Res. 14:1-40 (1985).
Gavezzotti, "Are Crystal Structures Predictable?" Acc. Chem. Res. 27:309-314 (1994).
Alaaeddine et al., "Production of the chemokine RANTES by articular chondrocytes and role in cartilage degradation," Arthritis Rheum. 44(7):1633-1643 (2001).
Iino et al., "Molecular cloning and functional characterization of Cynomolgus monkey (*Macaca fascicularis*) CC chemokine receptor, CCR3," Cytokine 19(6):276-286 (2002).
Katschke et al., "Differential expression of chemokine receptors on peripheral blood, synovial fluid, and synovial tissue monocytes/macrophages in rheumatoid arthritis," Arthritis. Rheum. 44(5):1022-1032 (2001).
White et al., "Identification of potent, selective non-peptide CC chemokine receptor-3 antagonist that inhibits eotaxin-, eotaxin-2-, and monocyte chemotactic protein-4-induced eosinophil migration," J. Biol. Chem. 275(47):36626-36631 (2000).
Vippagunta et al., "Crystalline solids," Adv. Drug Deliv. Rev. 48:3-26 (2001).
Abonyo et al., "Modulation of eotaxin-3 (CCL26) in alveolar type II epithelial cells," Cytokine 36:237-244 (2006).
Akashi et al., "A novel small-molecule compound targeting CCR5 and CXCR3 prevents acute and chronic allograft rejection," Transplantation 80:378-384 (2005).
Nakamura et al., "A specific CCR3 chemokine receptor antagonist inhibits both early and late phase allergic inflammation in the conjunctiva," Immunological Res. 33:213-221 (2005).
Sabroe et al., "A small molecule antagonist of chemokine receptors CCR1 and CCR3" J. Biol. Chem. 275 (34):25985-25992 (2000).
O'Driscoll, "Heavyweight drugs. Swapping selectred hydrogen atoms for deuterium could be a fast route to making safer, longer lasting drugs," Drug Discovery, Chemistry & Industry, Mar. 9, 2009, pp. 24-26.
Asgharnejad, "Improving oral drug transport via prodrugs," Transport Processes in Pharmaceutical Systems, Amidon et al., Eds., Marcell Dekker, Inc., New York, pp. 185-218 (2000).

(56) References Cited

OTHER PUBLICATIONS

Baillie, "The use of stable isotopes in pharmacological research," Pharmacol. Rev. 33(2):81-132 (1981).
Balant et al., "Prodrugs for the improvement of drug absorption via different routes of administration," Eur. J. Drug Metab. Pharmacokinet. 15(2):143-153 (1990).
Balimane et al., "Involvement of multiple transporters in the oral absorption of nucleoside analogues," Adv. Drug Del. Rev. 39:183-209 (1999).
Berge et al., "Pharmaceutical Salts," J. Pharm. Sci. 66, 1-19 (1977).
Bischoff et al., "Immunnohistological assessment of intestinal eosinophil activation in patients with eosinophilic gastroenteritis and inflammatory bowel disease," Am. J. Gastroenterol. 94:3521-3529 (199).
Browne, "Review: Forsphenytoin (Cerebyx)," Clin. Neurophamacol. 20(1):1-12 (1997).
Browne, "Stable isotope techniques in early drug development: an economic evaluation," J. Clin. Pharmacol. 38 (3):213-220 (1998).
Bundgaard, "Bioreversible derviatization of drugs— principle and applicability to improve the therapeutic effects of drugs," Arch. Pharm. Chem. 8:1-39 (1979).
Bundgaard, "Controlled Drug Delivery," International Symposium of the Association for Pharmaceutical Technology 17:179-196 ( 1984).
Bundgaard, "Means to enhance penetration, prodrugs as a a means to improve the delivery of peptide drugs," Adv. Drug Delivery Rev. 8:1-38 (1992).
Cherrah et al., "Study of deuterium isotope effects on protein binding by gas chromatography/mass spectrometry. Caffeine and deuterated isotopomers," Biomed. Environ. Mass Spectrom 14(11):653-357 (1987).
Combadiere et al., "Cloning and functional expression of a human eosinophil CC chemokine receptor," J. Biol. Chem. 270:16491-16494 (1995).
Durham et al., "Eosinophils, bronchial hyperreactivity and late-phase asthmatic reactions," Clin. Allergy 15:411-418 (1985).
Durham, "Mechanisms of mucosal inflammation in the nose and lungs," Clin. Exp. Allergy 28(Suppl. 2):11-16 (1998).
Dyck et al., "Effects of deuterium substitution on the catabolism of beta-phenylethylamine: an in vivo study," J. Neurochem. 46(2):399-404 (1986).
Evans et al., "Pretreatment with antibody to eosinophil major basic protein prevents hyperresponsiveness by protecting neuronal M2 muscarinic receptors in antigen-challenged guinea pigs," J. Clin. Invest. 100:2254-2262 (1997).
Farquhar et al., "Biologically reversible phosphate-protective groups," J. Pharm. Sci. 72(3):324-325 (1983).
Fleisher et al., "Design of prodrugs for improved gastrointestinal absorption by intestinal enzyme targeting," Methods Enzymol. 112:360-381 (1985).
Fleisher et al., "Improved oral drug delivery: solubility limitations overcome by the use of prodrugs," Adv. Drug Delivery Rev. 19:115-130 ( 1996).
Freeman et al., "Bioreversible protection for the phospho group: chemical stability and bioactivation of di(4-acetoxybenzyl) methylphyosphyonate with carboxyesterase," J. Chem. Soc. Chem. Commun. 875-877 (1991).
Friis and Bundgaard, "Prodrugs of phosphates and phosphonates: Novel lipophilic α-acyloxyalkyl ester derivatives of phosphate- or phosphonate containing drugs masking the negative charges of these groups," Eur. J. Pharm. Sci. 4 (1):49-59 ( 1996).
Fulkerson et al., "A central regulatory role for eosinophils and the eotaxin/CCR3 axis in chronic experimental allergic airway inflammation," Proc. Natl. Acad. Sci. USA 103:16418-16423 (2006).
Gangwar et al., "Prodrug strategies to enhance the intestinal absorption of peptides," Drug Discovery Today 2 (4):148-155 (1997).
Gouyette, "Synthesis of deuterium-labelled elliptinium and its use in metabolic studies," Biomed. Environ. Mass Spectrom. 15(5):243-247 (1988).

Grimaldi et al., "Depletion of eosinophils in mice through the use of antibodies specific for C-C chemokine receptor 3 (CCR3)," J. Leukoc. Biol. 65(6):846-853 (1999).
Harper et al., "Fortschritte der Arzneimittelforschung," Progress in Drug Research, Birkhauser Verlag Basel, vol. 4, pp. 221-294 (1962).
Haskins, "The application of stable isotopes in biomedical research," Biomed. Mass Spectrom 9(7):269-277 (1982).
Heath et al., "Chemokine receptor usage by human eosinophils. The importance of CCR3 demonstrated using an antagonistic monoclonal antibody," J. Clin. Invest. 99:178-184 (1997).
Higuchi et al., Des. Biopharm. Prop. Prodrugs Analogs 409-421 (1977).
Honma et al., "The metabolism of roxatidine acetate hydrochloride. Liberation of deuterium from the piperidine ring during hydroxylation," Drug Metab. Dispos. 15(4):551-559 (1987).
Humbles et al., "The murine CCR3 receptor regulates both the role of eosinophils and mast cells in allergen-induced airway inflammation and hyperresponsiveness," Proc. Natl. Acad. Sci. USA, 99:1479-1484 (2002).
Justice et al.,"Ablation of eosinophils leads to a reduction of allergen-induced pulmonary pathology," Am. J. Physiol. Lung Cell. Mol. Physiol., 284:L169-L178 (2003).
Kroegel et al., "Blood and bronchoalveolar eosinophils in allergic subjects after segmental antigen challenge: surface phenotype, density heterogeneity, and prostanoid production," J. Allergy Clin. Immunol. 93:725-734 (1994).
Leung, "Pathogenesis of atopic dermatitis," J. Allergy Clin. Immunol. 104:S99-108 (1999).
Ma et al., "CCR3 is essential for skin eosinophilia and airway hyperresponsiveness in a murine model of allergic skin inflammation," J. Clin. Invest. 109:621-628 (2002).
Mizen and Burton, "The use of esters as prodrugs for oral delivery of β-lactam antibiotics," Pharm. Biotech. 11:345-365 (1998).
Nathwani and Wood, "Penicillins. A current review of their clinical pharmacology and therapeutic use," Drugs 45 (6):866-894 (1993).
Pauletti et al., "Improvement of oral peptide bioavailability: peptidomimetics and prodrug strategies," Adv. Drug Del. Rev. 27:235-256 (1997).
Pieniaszek et al., "Moricizine bioavailability via simultaneous, dual, stable isotope administration: bioequivalence implications", J. Clin. Pharmacol. 39(8):817-825 (1999).
Pope et al., "The eotaxin chemokines and CCR3 are fundamental regulators of allergen-induced pulmonary eosinophilia," J. Immunol. 175(8):5341-5350 (2005).
Post et al., "Molecular characterization of two murine eosinophil beta chemokine receptors," J. Immunol. 155 (11):5299-5305 (1995).
Santus and Baker, "Osmotic drug delivery, a review of the patent literature," J. Controlled Release, 35:1-21 (1995).
Sinhababu and Thakker, "Prodrugs of anticancer agents," Adv. Drug Delievery Rev. 19:241-273 (1996).
Stella et al., "Prodrugs. Do they have advantages in clinical practice?," Drugs 29(5):455-473 (1985).
Tan et al., "Development and optimization of anti-HIV nucleoside analogs and prodrugs: A review of their cellular pharmacology, structure-activity relationships and pharmacokinetics," Adv. Drug Deliv. Rev. 39(1-3):117-151 (1999).
Taylor, "Improved passive oral drug delivery via prodrugs," Adv. Drug Delivery Rev. 19:131-148 (1996).
Tonn et al., "Simultaneous analysis of diphenhydramine and a stable isotope analog (2H10)diphenhydramine using capillary gas chromatography with mass selective detection in biological fluids from chronically instrumented pregnant ewes," Biol. Mass Spectrom 22(11):633-642 (1993).
Verma et al., "Formulation aspects in the development of osmotically controlled oral drug delivery systems," J. Control. Release 79(1-3):7-27 (2002).

\* cited by examiner

ISOTOPICALLY ENRICHED ARYLSULFONAMIDE CCR3 ANTAGONISTS

CROSS-REFERENCE TO RELATED APPLICATIONS

This application is a continuation of U.S. application Ser. No. 14/020,597, filed Sep. 6, 2013, which claims the benefit of U.S. Provisional Patent Application Ser. No. 61/698,390, filed Sep. 7, 2012, the disclosure of each of which is incorporated herein by reference in its entirety.

FIELD

Provided herein are isotopically enriched arylsulfonamides that are useful for modulating CCR3 activity, and pharmaceutical compositions thereof. Also provided herein are methods of their use for treating, preventing, or ameliorating one or more symptoms of a CCR3-mediated disease, disorder, or condition.

BACKGROUND

CC chemokine receptor 3 (CCR3) is a seven-transmembrane G protein-coupled receptor, which binds to a variety of CC chemokines, including eotaxin (CCL11), eotaxin-2 (CCL24), eotaxin-3 (CCL26), MCP-3 (CCL7), MCP-4 (CCL13), and RANTES (CCL5). CCR3 is known to be a major chemokine receptor expressed on allergic inflammatory cells, including eosinophils, basophils, mast cells, and T helper 2-type CD4+ cells (Combadiere et al., *J. Biol. Chem.* 1995, 270, 16491-16494; Post et al., *J. Immunol.* 1995, 155, 5299-5305). Eosinophils have been implicated in the pathogenesis of a number of allergic diseases, such as bronchial asthma (Durham and Kay, *Clin. Allergy* 1985, 15, 411-418; Kroegel et al., *J. Allergy Clin. Immunol.* 1994, 93, 725-734), allergic rhinitis (Durham, *Clin. Exp. Allergy* 1998, 28 Suppl. 2, 11-16), atopic dermatitis (Leung, *J. Allergy Clin. Immunol.* 1999, 104, S99-108), and eosinophilic gastroenteritis (Bischoff et al., *Am. J. Gastro.* 1999, 94, 3521-3529). It has been demonstrated that activated eosinophils release major basic protein (MBP), which blocks inhibitory M2 muscarinic receptors (M2Rs) on nerves, increasing acetylcholine release and potentiating vagally mediated bronchoconstriction (Evans et al., *J. Clin. Invest.* 1997, 100, 2254-2262).

Numerous reports indicate that CCR3 plays important roles in allergic conditions. For example, it has been reported that, in both atopic and nonatopic asthma patients, there are increases in both mRNA and protein levels of CCR3 and its ligands, eotaxin, eotaxin-2, RANTES, and MCP-4 (Ying et al., *J. Immunol.* 1999, 99, 6321-6329). It has also been demonstrated that CCR3 gene deletion impairs eosinophil recruitment in an acute model of experimental asthma (Humbles et al., *Proc. Natl. Acad. Sci. USA* 2002, 99, 1479-1484; Ma et al., *J. Clin. Invest.* 2002, 109, 621-628; Pope et al., *J. Immunol.* 2005, 175, 5341-5350; Fulkerson et al., *Proc. Natl. Acad. Sci. USA* 2006, 103, 16418-16423). Furthermore, studies have shown that CCR3 antagonists, such as anti-CCR3 monoclonal antibodies, block binding of CCR3-ligands to either CCR3 transfectants or eosinophils, thus blocking chemotaxis of eosinophils induced by CC chemokines, such as eotaxin, RANTES, or MCP-3 (Heath et al., *J. Clin. Invest.* 1997, 99, 178-184; Grimaldi et al., *J. Leukocyte Biol.* 1999, 65, 846-853; Justice et al., *Am. J. Physiol.* 2003, 284, L168-L178). Therefore, CCR3 antagonists are potentially useful for the treatment of inflammatory diseases, such as allergic rhinitis and allergic asthma. In addition, CCR3 antagonists are also potentially useful for blocking infection of CCR3 expressing cells by certain microorganisms, such as HIV, as CCR3 is known to be an entry co-receptor for certain microorganisms.

SUMMARY OF THE DISCLOSURE

Provided herein is an arylsulfonamide of Formula I:

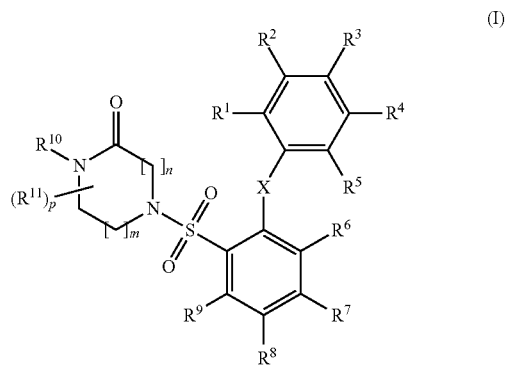

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof;

wherein:

$R^1$, $R^2$, $R^3$, $R^4$, $R^5$, and $R^8$ are each independently (a) hydrogen, deuterium, halo, cyano, nitro, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^6$, $R^7$, and $R^9$ are each independently (a) hydrogen or deuterium;

$R^{10}$ is (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{11}$ is (a) deuterium, halo, cyano, nitro, oxo, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or each pair of $R^{1b}$ and $R^{1c}$ together with the N atom to which they are attached independently form heteroaryl or heterocyclyl;

X is O or S;
m is an integer of 0, 1, 2, or 3;
n is an integer of 1, 2, or 3; and
p is an integer of 1, 2, 3, 4, 5, 6, 7, 8, 9, 10, 11, 12, 13, or 14;
wherein the arylsulfonamide is isotopically enriched;
wherein each alkyl, alkenyl, alkynyl, cycloalkyl, aryl, aralkyl, heterocyclyl, and heteroaryl is optionally substituted with one or more substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(NR$^a$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) each pair of R$^b$ and R$^e$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) each pair of R$^f$ and R$^g$ together with the N atom to which they are attached form heterocyclyl.

Also provided herein are pharmaceutical compositions comprising a compound disclosed herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable carriers.

Additionally provided herein is a method for treating, preventing, or ameliorating one or more symptoms of a CCR3-mediated disease, disorder, or condition in a subject, comprising administering to the subject a therapeutically effective amount of a compound disclosed herein, e.g., a compound of Formula I, an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

Furthermore, provided herein is a method for modulating CCR3 activity, comprising contacting a CCR3 with a therapeutically effective amount of a compound disclosed herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disease, disorder, or condition, or one or more of the symptoms associated with the disease, disorder, or condition; or alleviating or eradicating the cause(s) of the disease, disorder, or condition itself.

The terms "prevent," "preventing," and "prevention" are meant to include a method of delaying and/or precluding the onset of a disease, disorder, or condition, and/or its attendant symptoms; barring a subject from acquiring a disease, disorder, or condition; or reducing a subject's risk of acquiring a disease, disorder, or condition.

The term "therapeutically effective amount" are meant to include the amount of a compound that, when administered, is sufficient to prevent development of, or alleviate to some extent, one or more of the symptoms of the disease, disorder, or condition being treated. The term "therapeutically effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st ed.; Lippincott Williams & Wilkins: Philadelphia, Pa., 2005; *Handbook of Pharmaceu-* tical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disease, disorder, or condition. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a disease, disorder, or condition.

The term "alkyl" refers to a linear or branched saturated monovalent hydrocarbon radical, wherein the alkyl is optionally be substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, $C_{1-6}$ alkyl, including linear $C_{1-6}$ and branched $C_{3-6}$ alkyl, is also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkenyl" refers to a linear or branched monovalent hydrocarbon radical, which contains one or more, in one embodiment, one to five, in another embodiment, one, carbon-carbon double bond(s). In certain embodiments, the alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, in another embodiment, one, carbon-carbon triple bond(s). In certain embodiments, the alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic monovalent hydrocarbon radical, which is saturated or unsaturated, but non-aromatic. In certain embodiments, the cycloalkyl is bridged. In certain embodiments, the cycloalkyl is a fused ring group, e.g., a fused bicyclic group. In certain embodiments, the cycloalkyl is optionally substituted with one or more substituents Q as described herein. In certain embodiments, the cycloalkyl is a monocyclic, bicyclic, tricyclic, or tetracyclic ring system. In certain embodiments, the cycloalkyl is a cyclic monovalent hydrocarbon radical having from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "aryl" refers to a monovalent monocyclic aromatic group and/or monovalent polycyclic aromatic group that contain at least one aromatic carbon ring. In certain embodiments, the aryl is a monovalent aromatic group having from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. In certain embodiments, the aryl is a bicyclic or tricyclic carbon ring, where one of the rings is aromatic and the others of which may be saturated, partially unsaturated, or aromatic, for example, dihydronaphthyl, indenyl, indanyl, or tetrahydronaphthyl (tetralinyl). In certain embodiments, the aryl is optionally substituted with one or more substituents Q as described herein.

The term "aralkyl" or "arylalkyl" refers to a monovalent alkyl group substituted with one or more aryl groups. In certain embodiments, the aryl is a monocyclic, bicyclic, tricyclic, or tetracyclic ring system. In certain embodiments, the aralkyl is a monovalent alkyl group having from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, the aralkyl is optionally substituted with one or more substituents Q as described herein.

The term "heteroaryl" refers to a monovalent monocyclic aromatic group or monovalent polycyclic aromatic group that contains at least one aromatic ring, wherein at least one aromatic ring contains one or more heteroatoms independently selected from O, S, and N in the ring. In certain embodiments, the heteroaryl is bonded to the rest of a molecule through the aromatic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, the heteroaryl is a monocyclic, bicyclic, tricyclic, or tetracyclic ring system. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclyl has from 3 to 20, from 3 to 15, from 3 to 10, from 3 to 8, from 4 to 7, or from 5 to 6 ring atoms. In certain embodiments, the heterocyclyl is bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the rest of a molecule the main structure at any heteroatom or carbon atom, resulting in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclic is optionally substituted with one or more substituents Q as described herein.

The term "halogen", "halide," or "halo" refers to fluorine, chlorine, bromine, and/or iodine.

The term "optionally substituted" is intended to mean that a group or substituent, such as an alkyl, alkenyl, alkynyl, cycloalkyl, aryl, aralkyl, heteroaryl, and heterocyclyl group, may be substituted with one or more substituents Q, each of which is independently selected from, e.g., (a) deuterium, cyano (—CN), halo, nitro (—NO$_2$), and oxo (=O); (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q$^a$; or (iii) each pair of R$^b$ and R$^e$ together with the N atom to which they are attached form heterocyclyl, optionally substituted with one or more, in one embodiment, one, two, three, or four, substituents Q$^a$. As used herein, all groups that can be substituted are "optionally substituted," unless otherwise specified.

In one embodiment, each Q$^a$ is independently selected from the group consisting of (a) deuterium, cyano, halo, nitro, and oxo; and (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heteroaryl or heterocyclyl.

The terms "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemates of the compound in question.

In describing an optically active compound, the prefixes R and S are used to denote the absolute configuration of a compound about its chiral center(s). The (+) and (−) are used to denote the optical rotation of a compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen (H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an isotopically enriched compound is in an unstable form, that is, radioactive. In certain embodiments, an isotopically enriched compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, as example, or any carbon can be $^{13}$C, as example, or any nitrogen can be $^{15}$N, as example, or any oxygen can be $^{18}$O, as example.

The term "isotopic enrichment" refers to the percentage of incorporation of a less prevalent isotope (e.g., D) of an element at a given position in a molecule in the place of a more prevalent isotope (e.g., $^1$H) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium ($^1$H), deuterium ($^2$H or D), and tritium ($^3$H), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}$C) and carbon-13 ($^{13}$C) in their natural abundances. Carbon-12 is the most common carbon isotope having a natural abundance of more than 98.89%. Carbon-13 is a less prevalent hydrogen isotope having a natural abundance of about 1.11%.

The term "carbon-13 enrichment" or "$^{13}$C enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "naturally occurring" or "native" when used in connection with biological materials such as nucleic acid molecules, polypeptides, and host cells, refers to materials which are found in nature and are not manipulated by man. Similarly, "non-naturally occurring" or "non-native" refers to a material that is not found in nature or that has been structurally modified or synthesized by man.

The term "CCR3" refers to CC chemokine receptor 3 or a variant thereof, which is capable of mediating a cellular response to a variety of chemokines, including, but not limited to, eotaxin (CCL11), eotaxin-3 (CCL26), MCP-3 (CCL7), MCP-4 (CCL13), and RANTES (CCL5). CCR3 variants include proteins substantially homologous to a native CCR3, i.e., proteins having one or more naturally or non-naturally occurring amino acid deletions, insertions or substitutions (e.g., CCR3 derivatives, homologs, and fragments), as compared to the amino acid sequence of a native CCR3. The amino acid sequence of a CCR3 variant is at least about 80% identical, at least about 90% identical, or at least about 95% identical to a native CCR3.

The term "CCR3 antagonist" refers to a compound that, e.g., partially or totally blocks, decreases, prevents, inhibits, or downregulates CCR3 activity. The term "CCR3 antagonist" also refers to a compound that binds to, delays the activation of, inactivates, or desensitizes a CCR3 receptor. A CCR3 antagonist may act by interfering with the interaction of a CCR3 receptor and its chemokine ligand, including, but not limited to, eotaxin (CCL11), eotaxin-3 (CCL26), MCP-3 (CCL7), MCP-4 (CCL13), and/or RANTES (CCL5).

The terms "CCR3-mediated disease, disorder, or condition" and "a disease, disorder, or condition mediated by CCR3" refer to a disease, disorder, or condition characterized by abnormal or dysregulated, e.g., greater than normal, CCR3 activity. Abnormal CCR3 functional activity might arise as the result of CCR3 overexpression in cells, expression of CCR3 in cells which normally do not express CCR3, or CCR3 dysregulation in cells (e.g., due to constitutively activation), leading to, e.g., inflammatory and immune-related disorders or diseases. A CCR3-mediated condition, disorder or disease may be completely or partially mediated by abnormal or dysregulated CCR3 activity. In particular, a CCR3-mediated condition, disorder or disease is one in which modulation of a CCR3 receptor results in some effect on the underlying condition or disorder, e.g., a CCR3 antagonist results in some improvement in at least some of patients being treated.

The phrase "an enantiomer, a mixture of enantiomers, a mixture of two or more diastereomers, a tautomer, or a mixture of two or more tautomers thereof; or a pharmaceutically acceptable salt, solvate, hydrate, or prodrug thereof" has the same meaning as the phrase "an enantiomer, a mixture of enantiomers, a mixture of two or more diastereomers, a tautomer, or a mixture of two or more tautomers of the compound referenced therein; a pharmaceutically acceptable salt, solvate, hydrate, or prodrug of the compound referenced therein; or a pharmaceutically acceptable salt, solvate, hydrate, or prodrug of an enantiomer, a mixture of enantiomers, a mixture of two or more diastereomers, a tautomer, or a mixture of two or more tautomers of the compound referenced therein."

Compounds

In one embodiment, provided herein is an arylsulfonamide of Formula I:

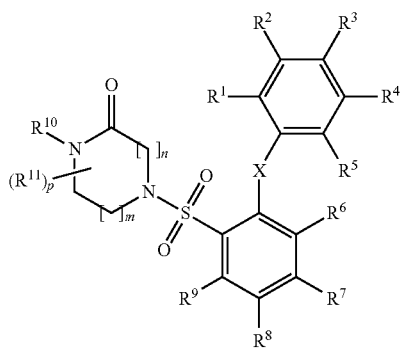

(I)

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof;

wherein:

$R^1$, $R^2$, $R^3$, $R^4$, $R^5$, and $R^8$ are each independently (a) hydrogen, deuterium, halo, cyano, nitro, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^6$, $R^7$, and $R^9$ are each independently (a) hydrogen or deuterium;

$R^{10}$ is (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

$R^{11}$ is (a) deuterium, halo, cyano, nitro, oxo, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$) N$R^{1b}R^{1c}$, —O$R^{1a}$, —OC(O)$R^{1a}$, —OC(O)O$R^{1a}$, —OC(O) N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C (O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$ S(O)N$R^{1b}R^{1c}$, —N$R^{1a}$ S(O)$_2$N$R^{1b}R^{1c}$, —S$R^{1a}$, —S(O)$R^{1a}$, —S(O)$_2R^{1a}$, —S(O) N$R^{1b}R^{1c}$, or —S(O)$_2$N$R^{1b}R^{1c}$;

each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or each pair of $R^{1b}$ and $R^{1c}$ together with the N atom to which they are attached independently form heteroaryl or heterocyclyl;

X is O or S;

m is an integer of 0, 1, 2, or 3;

n is an integer of 1, 2, or 3; and p is an integer of 1, 2, 3, 4, 5, 6, 7, 8, 9, 10, 11, 12, 13, or 14;

wherein the arylsulfonamide is isotopically enriched;

wherein each alkyl, alkenyl, alkynyl, cycloalkyl, aryl, aralkyl, heterocyclyl, and heteroaryl is optionally substituted with one or more substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$) N$R^bR^c$, —O$R^a$, —OC(O)$R^a$, —OC(O)O$R^a$, —OC(O) N$R^bR^c$, —OC(N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O) $R^d$, —N$R^a$C(O)O$R^d$, —N$R^a$C(O)N$R^bR^c$, —N$R^a$C(N$R^d$) N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O) N$R^bR^c$, and —S(O)$_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) each pair of $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) each pair of R$^f$ and R$^g$ together with the N atom to which they are attached form heterocyclyl.

In one embodiment, in Formula I, $R^1$, $R^2$, $R^3$, $R^4$, and $R^5$ are each independently hydrogen, deuterium, halo, or $C_{1-6}$ alkyl optionally substituted with one or more substituents Q;

$R^6$, $R^7$, and $R^9$ are each independently hydrogen or deuterium;

$R^8$ is cyano or nitro;

$R^{10}$ is (a) hydrogen or deuterium; (b) $C_{1-6}$ alkyl or $C_{3-7}$ cycloalkyl, each optionally substituted with one or more substituents Q; or (c) —C(O)R$^{1a}$, —C(O)NR$^{1b}$R$^{1c}$, or —S(O)$_2$R$^{1a}$; wherein R$^{1a}$ and R$^{1c}$ are each independently $C_{1-6}$ alkyl; $C_{3-7}$ cycloalkyl, optionally substituted with one or two $C_{1-6}$ alkyl; or $C_{6-14}$ aryl, optionally substituted with one or more halo or $C_{1-6}$ alkyl, where the alkyl is further optionally substituted with one, two, or three halo; and R$^{1b}$ is hydrogen or deuterium;

each $R^{11}$ is independently deuterium or $C_{1-6}$ alkyl optionally substituted with one or more substituents Q;

X is O or S;

m is an integer of 0, 1, or 2;

n is an integer of 1 or 2; and p is an integer of 1, 2, 3, 4, 5, 6, 7, 8, 9, or 10.

In another embodiment, in Formula I, $R^1$, $R^2$, $R^3$, $R^4$, and $R^5$ are each independently hydrogen, deuterium, halo, or $C_{1-6}$ alkyl optionally substituted with one or more substituents Q;

$R^6$, $R^7$, and $R^9$ are each independently hydrogen or deuterium;

$R^8$ is cyano or nitro;

$R^{10}$ is hydrogen or deuterium;

each $R^{11}$ is independently deuterium or $C_{1-6}$ alkyl optionally substituted with one or more substituents Q;

X is O or S;

m is an integer of 0, 1, or 2;

n is an integer of 1 or 2; and p is an integer of 1, 2, 3, 4, 5, 6, 7, 8, 9, or 10.

In yet another embodiment, in Formula I, $R^1$, $R^2$, $R^3$, $R^4$, and $R^5$ are each independently hydrogen, deuterium, chloro, or methyl;

$R^6$, $R^7$, and $R^9$ are each independently hydrogen or deuterium;

$R^8$ is cyano or nitro;

$R^{10}$ is hydrogen, deuterium, methyl, —CD$_3$, cyclopentyl, —C(O)R$^{1a}$, —C(O)NR$^{1b}$R$^{1c}$, or —S(O)$_2$R$^{1a}$; wherein R$^{1a}$ and R$^{1c}$ are each independently methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), cyclobutyl, cyclopentyl, cyclohexyl, dimethylbicyclo[2.2.1]heptyl (e.g., 7,7-dimethylbicyclo[2.2.1]-heptyl), phenyl, fluorophenyl (e.g., 2-fluorophenyl, 3-fluorophenyl, or 4-fluorophenyl), chlorophenyl (e.g., 2-chlorophenyl, 3-chlorophenyl, or 4-chlorophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), or ethylphenyl (e.g., 2-ethylphenyl, 3-ethylphenyl, or 4-ethylphenyl); and R$^{1b}$ is hydrogen or deuterium;

$R^{11}$ is deuterium;

X is O or S;

m is an integer of 0, 1, or 2;

n is an integer of 1 or 2; and p is an integer of 1, 2, 3, 4, 5, 6, 7, 8, 9, or 10.

In yet another embodiment, in Formula I, $R^1$, $R^3$, $R^5$, $R^6$, $R^7$, and $R^9$ are each independently hydrogen or deuterium;

$R^2$ and $R^4$ are each independently chloro or methyl;

$R^8$ is cyano;

$R^{10}$ is hydrogen, deuterium, methyl, —CD$_3$, cyclopentyl, —C(O)R$^{1a}$, —C(O)NR$^{1b}$R$^{1c}$, or —S(O)$_2$R$^{1a}$; wherein R$^{1a}$ and R$^{1c}$ are each independently methyl, ethyl, isopropyl, isobutyl, t-butyl, 1,1-dimethylpropyl, 2,2-dimethylpropyl, cyclobutyl, cyclopentyl, cyclohexyl, (1S,2S,4R)-7,7-dimethylbicyclo[2.2.1]-heptyl, phenyl, 2-chlorophenyl, 4-chlorophenyl, 2-fluorophenyl, 3-fluorophenyl, 4-fluorophenyl, 2-methylphenyl, 3-methylphenyl, 4-methylphenyl, 4-trifluoromethylphenyl, or 4-ethylphenyl; and R$^b$ is hydrogen or deuterium;

$R^{11}$ is deuterium;

X is O or S;

m is an integer of 1;

n is an integer of 1; and p is an integer of 1, 2, 3, 4, 5, or 6.

In yet another embodiment, in Formula I, $R^1$, $R^3$, $R^5$, $R^6$, $R^7$, and $R^9$ are each independently hydrogen or deuterium;

$R^2$ and $R^4$ are each independently chloro or methyl;

$R^8$ is cyano;

$R^{10}$ is hydrogen or deuterium;

$R^{11}$ is deuterium;

X is O or S;

m is an integer of 1;

n is an integer of 1; and p is an integer of 1, 2, 3, 4, 5, or 6.

In still another embodiment, in Formula I, $R^1$, $R^3$, $R^5$, $R^6$, $R^7$, and $R^9$ are each independently hydrogen or deuterium;

$R^2$ and $R^4$ are chloro;

$R^8$ is cyano;

$R^{10}$ is hydrogen or deuterium;

$R^{11}$ is deuterium;

X is O or S;

m is an integer of 1;

n is an integer of 1; and p is an integer of 1, 2, 3, 4, 5, or 6.

In another embodiment, provided herein is an arylsulfonamide of Formula II:

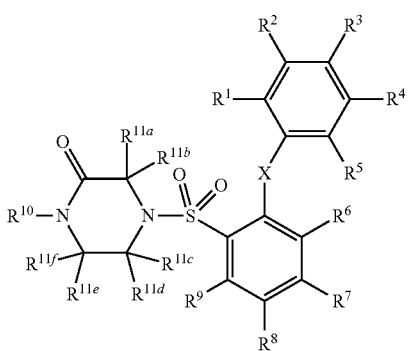

(II)

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof;
wherein:

$R^{11a}$, $R^{11b}$, $R^{11c}$, $R^{11d}$, $R^{11e}$, and $R^{11f}$ are each independently hydrogen or deuterium; and $R^1$, $R^2$, $R^3$, $R^4$, $R^5$, $R^6$, $R^7$, $R^8$, $R^9$, $R^{10}$, and X are each as defined herein;

wherein the arylsulfonamide is isotopically enriched.

In one embodiment, in Formula II, $R^1$, $R^2$, $R^3$, $R^4$, and $R^5$ are each independently hydrogen, deuterium, halo, or $C_{1-6}$ alkyl optionally substituted with one or more substituents Q;

$R^6$, $R^7$, $R^9$, $R^{11a}$, $R^{11b}$, $R^{11c}$, $R^{11d}$, $R^{11e}$, and $R^{11f}$ are each independently hydrogen or deuterium;

$R^8$ is cyano or nitro;

$R^{10}$ is (a) hydrogen or deuterium; (b) $C_{1-6}$ alkyl or $C_{3-7}$ cycloalkyl, each of optionally substituted with one or more substituents Q; or (c) —C(O)$R^{1a}$, —C(O)NR$^{1b}R^{1c}$, or —S(O)$_2R^{1a}$; wherein $R^{1a}$ and $R^{1c}$ are each independently $C_{1-6}$ alkyl; $C_{3-7}$ cycloalkyl, optionally substituted with one or two $C_{1-6}$ alkyl; or $C_{6-14}$ aryl, optionally substituted with one or more halo or $C_{1-6}$ alkyl, where the alkyl is further optionally substituted with one, two, or three halo; and $R^{1b}$ is hydrogen or deuterium; and X is O or S.

In another embodiment, in Formula II, $R^1$, $R^2$, $R^3$, $R^4$, and $R^5$ are each independently hydrogen, deuterium, halo, or $C_{1-6}$ alkyl optionally substituted with one or more substituents Q;

$R^6$, $R^7$, $R^9$, $R^{10}$, $R^{11a}$, $R^{11b}$, $R^{11c}$, $R^{11d}$, $R^{11e}$, and $R^{11f}$ are each independently hydrogen or deuterium;

$R^8$ is cyano or nitro; and

X is O or S.

In yet another embodiment, in Formula II, $R^1$, $R^2$, $R^3$, $R^4$, and $R^5$ are each independently hydrogen, deuterium, chloro, or methyl;

$R^6$, $R^7$, $R^9$, $R^{11a}$, $R^{11b}$, $R^{11c}$, $R^{11d}$, $R^{11e}$, and $R^{11f}$ are each independently hydrogen or deuterium;

$R^8$ is cyano or nitro;

$R^{10}$ is hydrogen, deuterium, methyl, —CD$_3$, cyclopentyl, —C(O)$R^{1a}$, —C(O)NR$^{1b}R^{1c}$, or —S(O)$_2R^{1a}$; wherein $R^{1a}$ and $R^{1c}$ are each independently methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), cyclobutyl, cyclopentyl, cyclohexyl, dimethylbicyclo[2.2.1]heptyl (e.g., 7,7-dimethylbicyclo[2.2.1]-heptyl), phenyl, fluorophenyl (e.g., 2-fluorophenyl, 3-fluorophenyl, or 4-fluorophenyl), chlorophenyl (e.g., 2-chlorophenyl, 3-chlorophenyl, or 4-chlorophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), or ethylphenyl (e.g., 2-ethylphenyl, 3-ethylphenyl, or 4-ethylphenyl); and $R^{1b}$ is hydrogen or deuterium; and X is O or S.

In yet another embodiment, in Formula II, $R^1$, $R^3$, $R^5$, $R^6$, $R^7$, $R^9$, $R^{11a}$, $R^{11b}$, $R^{11c}$, $R^{11d}$, $R^{11e}$, and $R^{11f}$ are each independently hydrogen or deuterium;

$R^2$ and $R^4$ are each independently chloro or methyl;

$R^8$ is cyano;

$R^{10}$ is hydrogen, deuterium, methyl, —CD$_3$, cyclopentyl, —C(O)$R^a$, —C(O)NR$^{1b}R^{1c}$, or —S(O)$_2R^{1a}$; wherein $R^{1a}$ and $R^{1c}$ are each independently methyl, ethyl, isopropyl, isobutyl, t-butyl, 1,1-dimethylpropyl, 2,2-dimethylpropyl, cyclobutyl, cyclopentyl, cyclohexyl, (1S,2S,4R)-7,7-dimethylbicyclo[2.2.1]-heptyl, phenyl, 2-chlorophenyl, 4-chlorophenyl, 2-fluorophenyl, 4-fluorophenyl, 2-methylphenyl, 3-methylphenyl, 4-methylphenyl, 4-trifluoromethylphenyl, or 4-ethylphenyl; and $R^{1b}$ is hydrogen or deuterium; and X is O or S.

In yet another embodiment, in Formula II, $R^1$, $R^3$, $R^5$, $R^6$, $R^7$, $R^9$, $R^{10}$, $R^{11a}$, $R^{11b}$, $R^{11c}$, $R^{11d}$, $R^{11e}$, and $R^{11f}$ are each independently hydrogen or deuterium;

$R^2$ and $R^4$ are each independently chloro or methyl;

$R^8$ is cyano; and

X is O or S.

In still another embodiment, in Formula II, $R^1$, $R^3$, $R^5$, $R^6$, $R^7$, $R^9$, $R^{10}$, $R^{11a}$, $R^{11b}$, $R^{11c}$, $R^{11d}$, $R^{11e}$, and $R^{11f}$ are each independently hydrogen or deuterium;

$R^2$ and $R^4$ are chloro;

$R^8$ is cyano; and

X is O or S.

In yet another embodiment, provided herein is an arylsulfonamide of Formula III:

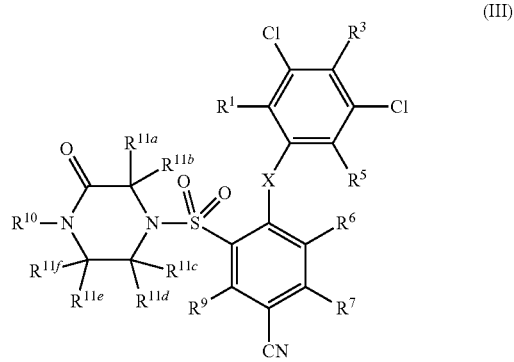

(III)

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof; wherein $R^1$, $R^3$, $R^5$, $R^6$, $R^7$, $R^9$, $R^{10}$, $R^{11a}$, $R^{11b}$, $R^{11c}$, $R^{11d}$, $R^{11e}$, $R^{11f}$, and X are each as defined herein; and wherein the arylsulfonamide is isotopically enriched.

In still another embodiment, provided herein is an arylsulfonamide of Formula IV:

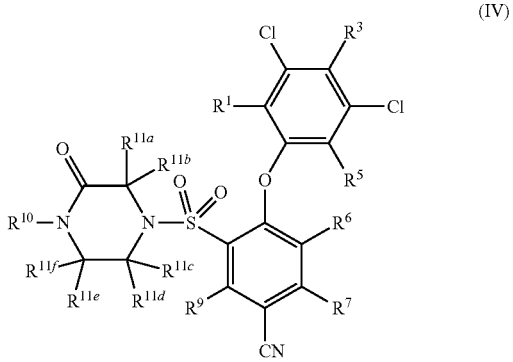

(IV)

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof; wherein $R^1$, $R^3$, $R^5$, $R^6$, $R^7$, $R^9$, $R^{10}$, $R^{11a}$, $R^{11b}$, $R^{11c}$, $R^{11d}$, $R^{11e}$, and $R^{11f}$ are each as defined herein; and wherein the arylsulfonamide is isotopically enriched.

The groups, $R^1$, $R^2$, $R^3$, $R^4$, $R^5$, $R^6$, $R^7$, $R^8$, $R^9$, $R^{10}$, $R^{11}$, $R^{1a}$, $R^{1b}$, $R^{1c}$, $R^{1d}$, $R^{11a}$, $R^{11a}$, $R^{11b}$, $R^{11c}$, $R^{11d}$, $R^{11e}$, $R^{11f}$, X, m, n, and p in formulae described herein, including Formulae I to IV, are further defined in the embodiments described herein. All combinations of the embodiments provided herein for such groups are within the scope of this disclosure.

In certain embodiments, $R^1$ is hydrogen. In certain embodiments, $R^1$ is deuterium. In certain embodiments, $R^1$ is halo. In certain embodiments, $R^1$ is fluoro, chloro, bromo, or iodo. In certain embodiments, $R^1$ is fluoro. In certain embodiments, $R^1$ is chloro. In certain embodiments, $R^1$ is cyano. In certain embodiments, $R^1$ is —$^{13}$CN. In certain embodiments, $R^1$ is nitro. In certain embodiments, $R^1$ is guanidine. In certain embodiments, $R^1$ is $C_{1-6}$ alkyl, optionally substituted with one or more substituents Q. In certain embodiments, $R^1$ is $C_{1-6}$ alkyl, optionally substituted with one, two, or three halo. In certain embodiments, $R^1$ is methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^1$ is methyl, —$CH_2D$, —$CHD_2$, or —$CD_3$. In certain embodiments, $R^1$ is $C_{2-6}$ alkenyl, optionally substituted with one or more substituents Q. In certain embodiments, $R^1$ is $C_{2-6}$ alkynyl, optionally substituted with one or more substituents Q. In certain embodiments, $R^1$ is $C_{3-7}$ cycloalkyl, optionally substituted with one or more substituents Q. In certain embodiments, $R^1$ is $C_{6-14}$ aryl, optionally substituted with one or more substituents Q. In certain embodiments, $R^1$ is $C_{7-15}$ aralkyl, optionally substituted with one or more substituents Q. In certain embodiments, $R^1$ is heteroaryl, optionally substituted with one or more substituents Q. In certain embodiments, $R^1$ is heterocyclyl, optionally substituted with one or more substituents Q.

In certain embodiments, $R^1$ is —$C(O)R^{1a}$, wherein $R^{1a}$ is as defined herein. In certain embodiments, $R^1$ is —$C(O)OR^{1a}$, wherein $R^{1a}$ is as defined herein. In certain embodiments, $R^1$ is —$C(O)NR^{1b}R^{1c}$, wherein $R^{1b}$ and $R^{1c}$ are each as defined herein. In certain embodiments, $R^1$ is —$C(NR^{1a})NR^{1b}R^{1c}$, wherein $R^{1a}$, $R^{1b}$, and $R^{1c}$ are each as defined herein. In certain embodiments, $R^1$ is —$OR^{1a}$, wherein $R^{1a}$ is as defined herein. In certain embodiments, $R^1$ is —$OR^{1a}$, wherein $R^{1a}$ is $C_{1-6}$ alkyl, optionally substituted with one or more substituents Q. In certain embodiments, $R^1$ is —$OR^{1a}$, wherein $R^{1a}$ is $C_{1-6}$ alkyl, optionally substituted with one, two, or three halo. In certain embodiments, $R^1$ is —$OC(O)R^{1a}$, wherein $R^{1a}$ is as defined herein. In certain embodiments, $R^1$ is —$OC(O)OR^{1a}$, wherein $R^{1a}$ is as defined herein. In certain embodiments, $R^1$ is —$OC(O)NR^{1b}R^{1c}$, wherein $R^{1b}$ and $R^{1c}$ are each as defined herein. In certain embodiments, $R^1$ is —$OC(=NR^{1a})NR^{1b}R^{1c}$, wherein $R^{1a}$, $R^{1b}$, and $R^{1c}$ are each as defined herein. In certain embodiments, $R^1$ is —$OS(O)R^{1a}$, wherein $R^{1a}$ is as defined herein. In certain embodiments, $R^1$ is —$OS(O)_2R^{1a}$, wherein $R^{1a}$ is as defined herein. In certain embodiments, $R^1$ is —$OS(O)NR^{1b}R^{1c}$, wherein $R^{1b}$ and $R^{1c}$ are each as defined herein. In certain embodiments, $R^1$ is —$OS(O)_2NR^{1b}R^{1c}$, wherein $R^{1b}$ and $R^{1c}$ are each as defined herein. In certain embodiments, $R^1$ is —$NR^{1b}R^{1c}$, wherein $R^{1b}$ and $R^{1c}$ are each as defined herein. In certain embodiments, $R^1$ is —$NR^{1a}C(O)R^{1d}$, wherein $R^{1a}$ and $R^{1d}$ are each as defined herein. In certain embodiments, $R^1$ is —$NR^{a}C(O)OR^{1d}$, wherein $R^{a}$ and $R^{d}$ are each as defined herein. In certain embodiments, $R^1$ is —$NR^{1a}C(O)NR^{1b}R^{1c}$, wherein $R^{1a}$, $R^{1b}$, and $R^{1c}$ are each as defined herein. In certain embodiments, $R^1$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, R is —$NR^{1a}S(O)R^{1d}$, wherein $R^{1a}$ and $R^{1d}$ are each as defined herein. In certain embodiments, R is —$NR^{1a}S(O)_2R^{1d}$, wherein $R^{1a}$ and $R^{1d}$ are each as defined herein. In certain embodiments, R is —$NR^{1a}S(O)NR^{1b}R^{1c}$, wherein $R^{1a}$, $R^{1b}$, and $R^{1c}$ are each as defined herein. In certain embodiments, $R^1$ is —$NR^{1a}S(O)_2NR^{1b}R^{1c}$, wherein $R^{1a}$, $R^{1b}$, and $R^{1c}$ are each as defined herein. In certain embodiments, $R^1$ is —$SR^{1a}$, wherein $R^{1a}$ is as defined herein. In certain embodiments, $R^1$ is —$SR^{1a}$, wherein $R^{1a}$ is $C_{1-6}$ alkyl, optionally substituted with one or more substituents Q. In certain embodiments, $R^1$ is —$SR^{1a}$, wherein $R^{1a}$ is $C_{1-6}$ alkyl, optionally substituted with one, two, or three halo. In certain embodiments, $R^1$ is —$S(O)R^{1a}$, wherein $R^{1a}$ is as defined herein. In certain embodiments, $R^1$ is —$S(O)_2R^{1a}$, wherein $R^{1a}$ is as defined herein. In certain embodiments, $R^1$ is —$S(O)NR^{1b}R^{1c}$, wherein $R^{1b}$ and $R^{1c}$ are each as defined herein. In certain embodiments, $R^1$ is —$S(O)_2NR^{1b}R^{1c}$, wherein $R^{1b}$ and $R^{1c}$ are each as defined herein.

In certain embodiments, $R^2$ is hydrogen. In certain embodiments, $R^2$ is deuterium. In certain embodiments, $R^2$ is halo. In certain embodiments, $R^2$ is fluoro, chloro, bromo, or iodo. In certain embodiments, $R^2$ is fluoro. In certain embodiments, $R^2$ is chloro. In certain embodiments, $R^2$ is cyano. In certain embodiments, $R^2$ is —$^{13}$CN. In certain embodiments, $R^2$ is nitro. In certain embodiments, $R^2$ is guanidine. In certain embodiments, $R^2$ is $C_{1-6}$ alkyl, optionally substituted with one or more substituents Q. In certain embodiments, $R^2$ is $C_{1-6}$ alkyl, optionally substituted with one, two, or three halo. In certain embodiments, $R^2$ is methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^2$ is methyl, —$CH_2D$, —$CHD_2$, or —$CD_3$. In certain embodiments, $R^2$ is $C_{2-6}$ alkenyl, optionally substituted with one or more substituents Q. In certain embodiments, $R^2$ is $C_{2-6}$ alkynyl, optionally substituted with one or more substituents Q. In certain embodiments, $R^2$ is $C_{3-7}$ cycloalkyl, optionally substituted with one or more substituents Q. In certain embodiments, $R^2$ is $C_{6-14}$ aryl, optionally substituted with one or more substituents Q. In certain embodiments, $R^2$ is $C_{7-15}$ aralkyl, optionally substituted with one or more substituents Q. In certain embodiments, $R^2$ is heteroaryl, optionally substituted with one or more substituents Q. In certain embodiments, $R^2$ is heterocyclyl, optionally substituted with one or more substituents Q.

In certain embodiments, $R^2$ is —C(O)$R^a$, wherein $R^{1a}$ is as defined herein. In certain embodiments, $R^2$ is —C(O)OR$^{1a}$, wherein $R^{1a}$ is as defined herein. In certain embodiments, $R^2$ is —C(O)NR$^{1b}$R$^{1c}$, wherein $R^{1a}$, $R^{1b}$ and $R^{1c}$ are each as defined herein. In certain embodiments, $R^2$ is —C(NR$^{1a}$)NR$^{1b}$R$^c$, wherein $R^{1a}$, $R^{1b}$, and $R^{1c}$ are each as defined herein. In certain embodiments, $R^2$ is —OR$^{1a}$, wherein $R^{1a}$ is as defined herein. In certain embodiments, $R^2$ is —OR$^{1a}$, wherein $R^{1a}$ is $C_{1-6}$ alkyl, optionally substituted with one or more substituents Q. In certain embodiments, $R^2$ is —OR$^{1a}$, wherein $R^{1a}$ is $C_{1-6}$ alkyl, optionally substituted with one, two, or three halo. In certain embodiments, $R^2$ is —OC(O)R$^{1a}$, wherein $R^{1a}$ is as defined herein. In certain embodiments, $R^2$ is —OC(O)OR$^{1a}$, wherein $R^{1a}$ is as defined herein. In certain embodiments, $R^2$ is —OC(O)NR$^{1b}$R$^{1c}$, wherein $R^{1b}$ and $R^{1c}$ are each as defined herein. In certain embodiments, $R^2$ is —OC(=NR$^{1a}$)NR$^{1b}$R$^{1c}$, wherein $R^{1a}$, $R^{1b}$, and $R^{1c}$ are each as defined herein. In certain embodiments, $R^2$ is —OS(O)R$^{1a}$, wherein $R^{1a}$ is as defined herein. In certain embodiments, $R^2$ is —OS(O)$_2$R$^{1a}$, wherein $R^{1a}$ is as defined herein. In certain embodiments, $R^2$ is —OS(O)NR$^{1b}$R$^{1c}$, wherein $R^{1b}$ and $R^{1c}$ are each as defined herein. In certain embodiments, $R^2$ is —OS(O)$_2$NR$^{1b}$R$^{1c}$, wherein $R^{1b}$ and $R^{1c}$ are each as defined herein. In certain embodiments, $R^2$ is —NR$^{1b}$R$^{1c}$, wherein $R^{1b}$ and $R^{1c}$ are each as defined herein. In certain embodiments, $R^2$ is —NR$^{1a}$C(O)R$^{1d}$, wherein $R^{1a}$ and $R^{1d}$ are each as defined herein. In certain embodiments, $R^2$ is —NR$^{1a}$C(O)OR$^{1d}$, wherein $R^{1a}$ and $R^{1d}$ are each as defined herein. In certain embodiments, $R^2$ is —NR$^{1a}$C(O)NR$^{1b}$R$^{1c}$, wherein $R^{1a}$, $R^{1b}$, and $R^{1c}$ are each as defined herein. In certain embodiments, $R^2$ is —NR$^{1a}$C(=NR$^{1d}$)NR$^{1b}$R$^{1c}$, wherein $R^{1a}$, $R^{1b}$, $R^{1c}$, and $R^{1d}$ are each as defined herein. In certain embodiments, $R^2$ is —NR$^{1a}$S(O)R$^{1d}$, wherein $R^{1a}$ and $R^{1d}$ are each as defined herein. In certain embodiments, $R^2$ is —NR$^{1a}$S(O)$_2$R$^{1d}$, wherein $R^{1a}$ and $R^{1d}$ are each as defined herein. In certain embodiments, $R^2$ is —NR$^{1a}$S(O)NR$^{1b}$R$^{1c}$, wherein $R^{1a}$, $R^{1b}$, and $R^{1c}$ are each as defined herein. In certain embodiments, $R^2$ is —NR$^{1a}$S(O)$_2$NR$^{1b}$R$^{1c}$, wherein $R^{1a}$, $R^{1b}$, and $R^{1c}$ are each as defined herein. In certain embodiments, $R^2$ is —SR$^{1a}$, wherein $R^{1a}$ is as defined herein. In certain embodiments, $R^2$ is —SR$^{1a}$, wherein $R^{1a}$ is $C_{1-6}$ alkyl, optionally substituted with one or more substituents Q. In certain embodiments, $R^2$ is —SR$^{1a}$, wherein $R^{1a}$ is $C_{1-6}$ alkyl, optionally substituted with one, two, or three halo. In certain embodiments, $R^2$ is —S(O)R$^{1a}$, wherein $R^{1a}$ is as defined herein. In certain embodiments, $R^2$ is —S(O)$_2$R$^{1a}$, wherein $R^{1a}$ is as defined herein. In certain embodiments, $R^2$ is —S(O)NR$^{1b}$R$^{1c}$, wherein $R^{1b}$ and $R^{1c}$ are each as defined herein. In certain embodiments, $R^2$ is —S(O)$_2$NR$^{1b}$R$^{1c}$, wherein $R^{1b}$ and $R^{1c}$ are each as defined herein.

In certain embodiments, $R^3$ is hydrogen. In certain embodiments, $R^3$ is deuterium. In certain embodiments, $R^3$ is halo. In certain embodiments, $R^3$ is fluoro, chloro, bromo, or iodo. In certain embodiments, $R^3$ is fluoro. In certain embodiments, $R^3$ is chloro. In certain embodiments, $R^3$ is cyano. In certain embodiments, $R^3$ is —$^{13}$CN. In certain embodiments, $R^3$ is nitro. In certain embodiments, $R^3$ is guanidine. In certain embodiments, $R^3$ is $C_{1-6}$ alkyl, optionally substituted with one or more substituents Q. In certain embodiments, $R^3$ is $C_{1-6}$ alkyl, optionally substituted with one, two, or three halo. In certain embodiments, $R^3$ is methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^3$ is methyl, —CH$_2$D, —CHD$_2$, or —CD$_3$. In certain embodiments, $R^3$ is $C_{2-6}$ alkenyl, optionally substituted with one or more substituents Q. In certain embodiments, $R^3$ is $C_{2-6}$ alkynyl, optionally substituted with one or more substituents Q. In certain embodiments, $R^3$ is $C_{3-7}$ cycloalkyl, optionally substituted with one or more substituents Q. In certain embodiments, $R^3$ is $C_{6-14}$ aryl, optionally substituted with one or more substituents Q. In certain embodiments, $R^3$ is $C_{7-15}$ aralkyl, optionally substituted with one or more substituents Q. In certain embodiments, $R^3$ is heteroaryl, optionally substituted with one or more substituents Q. In certain embodiments, $R^3$ is heterocyclyl, optionally substituted with one or more substituents Q.

In certain embodiments, $R^3$ is —C(O)R$^{1a}$, wherein $R^{1a}$ is as defined herein. In certain embodiments, $R^3$ is —C(O)OR$^{1a}$, wherein $R^{1a}$ is as defined herein. In certain embodiments, $R^3$ is —C(O)NR$^{1b}$R$^{1c}$, wherein $R^{1b}$ and $R^{1c}$ are each as defined herein. In certain embodiments, $R^3$ is —C(NR$^{1a}$)NR$^{1b}$R$^{1c}$, wherein $R^{1a}$, $R^{1b}$, and $R^{1c}$ are each as defined herein. In certain embodiments, $R^3$ is —OR$^{1a}$, wherein $R^{1a}$ is as defined herein. In certain embodiments, $R^3$ is —OR$^{1a}$, wherein $R^{1a}$ is $C_{1-6}$ alkyl, optionally substituted with one or more substituents Q. In certain embodiments, $R^3$ is —OR$^{1a}$, wherein $R^{1a}$ is $C_{1-6}$ alkyl, optionally substituted with one, two, or three halo. In certain embodiments, $R^3$ is —OC(O)R$^{1a}$, wherein $R^{1a}$ is as defined herein. In certain embodiments, $R^3$ is —OC(O)OR$^{1a}$, wherein $R^{1a}$ is as defined herein. In certain embodiments, $R^3$ is —OC(O)NR$^{1b}$R$^{1c}$, wherein $R^{1b}$ and $R^{1c}$ are each as defined herein. In certain embodiments, $R^3$ is —OC(=NR$^{1a}$)NR$^{1b}$R$^{1c}$, wherein $R^{1a}$, $R^{1b}$, and $R^{1c}$ are each as defined herein. In certain embodiments, $R^3$ is —OS(O)R$^{1a}$, wherein $R^{1a}$ is as defined herein. In certain embodiments, $R^3$ is —OS(O)$_2$R$^{1a}$, wherein $R^{1a}$ is as defined herein. In certain embodiments, $R^3$ is —OS(O)NR$^{1b}$R$^{1c}$, wherein $R^{1b}$ and $R^{1c}$ are each as defined herein. In certain embodiments, $R^3$ is —OS(O)$_2$NR$^{1b}$R$^{1c}$, wherein $R^{1b}$ and $R^{1c}$ are each as defined herein. In certain embodiments, $R^3$ is —NR$^{1b}$R$^{1c}$, wherein $R^{1b}$ and $R^{1c}$ are each as defined herein. In certain embodiments, $R^3$ is —NR$^{1a}$C(O)R$^{1d}$, wherein $R^{1a}$ and $R^{1d}$ are each as defined herein. In certain embodiments, $R^3$ is —NR$^{1a}$C(O)OR$^{1d}$, wherein $R^{1a}$ and $R^{1d}$ are each as defined herein. In certain embodiments, $R^3$ is —NR$^{1a}$C(O)NR$^{1b}$R$^{1c}$, wherein $R^{1a}$, $R^{1b}$, and $R^{1c}$ are each as defined herein. In certain embodiments, $R^3$ is —NR$^{1a}$C(=NR$^{1d}$)NR$^{1b}$R$^{1c}$, wherein $R^{1a}$, $R^{1b}$, $R^{1c}$, and $R^{1d}$ are each as defined herein. In certain embodiments, $R^3$ is —NR$^{1a}$S(O)R$^{1d}$, wherein $R^{1a}$ and $R^{1d}$ are each as defined herein. In certain embodiments, $R^3$ is —NR$^{1a}$S(O)$_2$R$^{1d}$, wherein $R^a$ and $R^d$ are each as defined herein. In certain embodiments, $R^3$ is —NR$^{1a}$S(O)NR$^{1b}$R$^{1c}$, wherein $R^{1a}$, $R^{1b}$, and $R^{1c}$ are each as defined herein. In certain embodiments, $R^3$ is —NR$^{1a}$S(O)$_2$NR$^{1b}$R$^{1c}$, wherein $R^{1a}$, $R^{1b}$, and $R^{1c}$ are each as defined herein. In certain embodiments, $R^3$ is —SR$^{1a}$, wherein $R^{1a}$ is as defined herein. In certain embodiments, $R^3$ is —SR$^{1a}$, wherein $R^{1a}$ is $C_{1-6}$ alkyl, optionally substituted with one or more substituents Q. In certain embodiments, $R^3$ is —SR$^{1a}$, wherein $R^{1a}$ is $C_{1-6}$ alkyl, optionally substituted with one, two, or three halo. In certain embodiments, $R^3$ is —S(O)R$^{1a}$, wherein $R^{1a}$ is as defined herein. In certain embodiments, $R^3$ is —S(O)$_2$R$^{1a}$, wherein $R^{1a}$ is as defined herein. In certain embodiments, $R^3$ is —S(O)NR$^{1b}$R$^{1c}$, wherein $R^{1b}$ and $R^{1c}$ are each as defined herein. In certain embodiments, $R^3$ is $-S(O)_2NR^{1b}R^{1c}$, wherein $R^{1b}$ and $R^{1c}$ are each as defined herein.

In certain embodiments, $R^4$ is hydrogen. In certain embodiments, $R^4$ is deuterium. In certain embodiments, $R^4$ is halo. In certain embodiments, $R^4$ is fluoro, chloro, bromo, or iodo. In certain embodiments, $R^4$ is fluoro. In certain embodiments, $R^4$ is chloro. In certain embodiments, $R^4$ is cyano. In certain embodiments, $R^4$ is $-^{13}CN$. In certain embodiments, $R^4$ is nitro. In certain embodiments, $R^4$ is guanidine. In certain embodiments, $R^4$ is $C_{1-6}$ alkyl, optionally substituted with one or more substituents Q. In certain embodiments, $R^4$ is $C_{1-6}$ alkyl, optionally substituted with one, two, or three halo. In certain embodiments, $R^4$ is methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^4$ is methyl, $-CH_2D$, $-CHD_2$, or $-CD_3$. In certain embodiments, $R^4$ is $C_{2-6}$ alkenyl, optionally substituted with one or more substituents Q. In certain embodiments, $R^4$ is $C_{2-6}$ alkynyl, optionally substituted with one or more substituents Q. In certain embodiments, $R^4$ is $C_{3-7}$ cycloalkyl, optionally substituted with one or more substituents Q. In certain embodiments, $R^4$ is $C_{6-14}$ aryl, optionally substituted with one or more substituents Q. In certain embodiments, $R^4$ is $C_{7-15}$ aralkyl, optionally substituted with one or more substituents Q. In certain embodiments, $R^4$ is heteroaryl, optionally substituted with one or more substituents Q. In certain embodiments, $R^4$ is heterocyclyl, optionally substituted with one or more substituents Q.

In certain embodiments, $R^4$ is $-C(O)R^{1a}$, wherein $R^{1a}$ is as defined herein. In certain embodiments, $R^4$ is $-C(O)OR^{1a}$, wherein $R^{1a}$ is as defined herein. In certain embodiments, $R^4$ is $-C(O)NR^{1b}R^{1c}$, wherein $R^{1a}$, $R^{1b}$ and $R^{1c}$ are each as defined herein. In certain embodiments, $R^4$ is $-C(NR^{1a})NR^{1b}R^{1c}$, wherein $R^{1a}$, $R^{1b}$, and $R^{1c}$ are each as defined herein. In certain embodiments, $R^4$ is $-OR^{1a}$, wherein $R^{1a}$ is as defined herein. In certain embodiments, $R^4$ is $-OR^{1a}$, wherein $R^{1a}$ is $C_{1-6}$ alkyl, optionally substituted with one or more substituents Q. In certain embodiments, $R^4$ is $-OR^{1a}$, wherein $R^{1a}$ is $C_{1-6}$ alkyl, optionally substituted with one, two, or three halo. In certain embodiments, $R^4$ is $-OC(O)R^{1a}$, wherein $R^{1a}$ is as defined herein. In certain embodiments, $R^4$ is $-OC(O)OR^{1a}$, wherein $R^{1a}$ is as defined herein. In certain embodiments, $R^4$ is $-OC(O)NR^{1b}R^{1c}$, wherein $R^{1b}$ and $R^{1c}$ are each as defined herein. In certain embodiments, $R^4$ is $-OC(=NR^{1a})NR^{1b}R^{1c}$, wherein $R^{1a}$, $R^{1b}$, and $R^{1c}$ are each as defined herein. In certain embodiments, $R^4$ is $-OS(O)R^{1a}$, wherein $R^{1a}$ is as defined herein. In certain embodiments, $R^4$ is $-OS(O)_2R^{1a}$, wherein $R^{1a}$ is as defined herein. In certain embodiments, $R^4$ is $-OS(O)NR^{1b}R^{1c}$, wherein $R^{1b}$ and $R^{1c}$ are each as defined herein. In certain embodiments, $R^4$ is $-OS(O)_2NR^{1b}R^{1c}$, wherein $R^{1b}$ and $R^{1c}$ are each as defined herein. In certain embodiments, $R^4$ is $-NR^{1b}R^{1c}$, wherein $R^{1b}$ and $R^{1c}$ are each as defined herein. In certain embodiments, $R^4$ is $-NR^{1a}C(O)R^{1d}$, wherein R and $R^{1d}$ are each as defined herein. In certain embodiments, $R^4$ is $-NR^{1a}C(O)OR^{1d}$, wherein $R^{1a}$ and $R^{1d}$ are each as defined herein. In certain embodiments, $R^4$ is $-NR^{1a}C(O)NR^{1b}R^{1c}$, wherein $R^{1a}$, $R^{1b}$, and $R^{1c}$ are each as defined herein. In certain embodiments, $R^4$ is $-NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^4$ is $-NR^{1a}S(O)R^{1d}$, wherein $R^{1a}$ and $R^{1d}$ are each as defined herein. In certain embodiments, $R^4$ is $-NR^{1a}S(O)_2R^{1d}$, wherein $R^{1a}$ and $R^{1d}$ are each as defined herein. In certain embodiments, $R^4$ is $-NR^{a}S(O)NR^{1b}R^{1c}$, wherein $R^{1a}$, $R^{1b}$, and $R^{1c}$ are each as defined herein. In certain embodiments, $R^4$ is $-NR^{1a}S(O)_2NR^{1b}R^{1c}$, wherein $R^{1a}$, $R^{1b}$, and $R^{1c}$ are each as defined herein. In certain embodiments, $R^4$ is $-SR^{1a}$, wherein $R^{1a}$ is as defined herein. In certain embodiments, $R^4$ is $-SR^{1a}$, wherein $R^{1a}$ is $C_{1-6}$ alkyl, optionally substituted with one or more substituents Q. In certain embodiments, $R^4$ is $-SR^{1a}$, wherein $R^{1a}$ is $C_{1-6}$ alkyl, optionally substituted with one, two, or three halo. In certain embodiments, $R^4$ is $-S(O)R^{1a}$, wherein $R^{1a}$ is as defined herein. In certain embodiments, $R^4$ is $-S(O)_2R^{1a}$, wherein $R^{1a}$ is as defined herein. In certain embodiments, $R^4$ is $-S(O)NR^{1b}R^{1c}$, wherein $R^{1b}$ and $R^{1c}$ are each as defined herein. In certain embodiments, $R^4$ is $-S(O)_2NR^{1b}R^{1c}$, wherein $R^{1b}$ and $R^{1c}$ are each as defined herein.

In certain embodiments, $R^5$ is hydrogen. In certain embodiments, $R^5$ is deuterium. In certain embodiments, $R^5$ is halo. In certain embodiments, $R^5$ is fluoro, chloro, bromo, or iodo. In certain embodiments, $R^5$ is fluoro. In certain embodiments, $R^5$ is chloro. In certain embodiments, $R^5$ is cyano. In certain embodiments, $R^5$ is $-^{13}CN$. In certain embodiments, $R^5$ is nitro. In certain embodiments, $R^5$ is guanidine. In certain embodiments, $R^5$ is $C_{1-6}$ alkyl, optionally substituted with one or more substituents Q. In certain embodiments, $R^5$ is $C_{1-6}$ alkyl, optionally substituted with one, two, or three halo. In certain embodiments, $R^5$ is methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^5$ is methyl, $-CH_2D$, $-CHD_2$, or $-CD_3$. In certain embodiments, $R^5$ is $C_{2-6}$ alkenyl, optionally substituted with one or more substituents Q. In certain embodiments, $R^5$ is $C_{2-6}$ alkynyl, optionally substituted with one or more substituents Q. In certain embodiments, $R^5$ is $C_{3-7}$ cycloalkyl, optionally substituted with one or more substituents Q. In certain embodiments, $R^5$ is $C_{6-14}$ aryl, optionally substituted with one or more substituents Q. In certain embodiments, $R^5$ is $C_{7-15}$ aralkyl, optionally substituted with one or more substituents Q. In certain embodiments, $R^5$ is heteroaryl, optionally substituted with one or more substituents Q. In certain embodiments, $R^5$ is heterocyclyl, optionally substituted with one or more substituents Q.

In certain embodiments, $R^5$ is $-C(O)R^{1a}$, wherein $R^{1a}$ is as defined herein. In certain embodiments, $R^5$ is $-C(O)OR^{1a}$, wherein $R^{1a}$ is as defined herein. In certain embodiments, $R^5$ is $-C(O)NR^{1b}R^{1c}$, wherein $R^{1a}$, $R^{1b}$ and $R^{1c}$ are each as defined herein. In certain embodiments, $R^5$ is $-C(NR^{1a})NR^{1b}R^{1c}$, wherein $R^{1a}$, $R^{1b}$, and $R^{1c}$ are each as defined herein. In certain embodiments, $R^5$ is $-OR^{1a}$, wherein $R^{1a}$ is as defined herein. In certain embodiments, $R^5$ is $-OR^{1a}$, wherein $R^{1a}$ is $C_{1-6}$ alkyl, optionally substituted with one or more substituents Q. In certain embodiments, $R^5$ is $-OR^{1a}$, wherein $R^{1a}$ is $C_{1-6}$ alkyl, optionally substituted with one, two, or three halo. In certain embodiments, $R^5$ is $-OC(O)R^{1a}$, wherein $R^{1a}$ is as defined herein. In certain embodiments, $R^5$ is $-OC(O)OR^{1a}$, wherein $R^{1a}$ is as defined herein. In certain embodiments, $R^5$ is $-OC(O)NR^{1b}R^{1c}$, wherein $R^{1b}$ and $R^{1c}$ are each as defined herein. In certain embodiments, $R^5$ is $-OC(=NR^{1a})NR^{1b}R^{1c}$, wherein $R^{1a}$, $R^{1b}$, and $R^{1c}$ are each as defined herein. In certain embodiments, $R^5$ is $-OS(O)R^{1a}$, wherein $R^{1a}$ is as defined herein. In certain embodiments, $R^5$ is $-OS(O)_2R^{1a}$, wherein $R^{1a}$ is as defined herein. In certain embodiments, $R^5$ is $-OS(O)NR^{1b}R^{1c}$, wherein $R^{1b}$ and $R^{1c}$ are each as defined herein. In certain embodiments, $R^5$ is —OS(O)$_2$NR$^{1b}$R$^{1c}$, wherein R$^{1b}$ and R$^{1c}$ are each as defined herein. In certain embodiments, $R^5$ is —NR$^{1b}$R$^{1c}$, wherein R$^{1b}$ and R$^{1c}$ are each as defined herein. In certain embodiments, $R^5$ is —NR$^{1a}$C(O)R$^{1d}$, wherein R$^{1a}$ and R$^{1d}$ are each as defined herein. In certain embodiments, $R^5$ is —NR$^{1a}$C(O)OR$^{1d}$, wherein R$^{1a}$ and R$^{1d}$ are each as defined herein. In certain embodiments, $R^5$ is —NR$^{1a}$C(O)NR$^{1b}$R$^{1c}$, wherein R$^{1a}$, R$^{1b}$, and R$^{1c}$ are each as defined herein. In certain embodiments, $R^5$ is —NR$^{1a}$C(=NR$^{1d}$)NR$^{1b}$R$^{1c}$, wherein R$^{1a}$, R$^{1b}$, R$^{1c}$, and R$^{1d}$ are each as defined herein. In certain embodiments, $R^5$ is —NR$^{1a}$S(O)R$^{1d}$, wherein R$^{1a}$ and R$^{1d}$ are each as defined herein. In certain embodiments, $R^5$ is —NR$^{1a}$S(O)$_2$R$^{1d}$, wherein R$^{1a}$ and R$^{1d}$ are each as defined herein. In certain embodiments, R is —NR$^{1a}$S(O)NR$^{1b}$R$^{1c}$, wherein R$^{1a}$, R$^{1b}$, and R$^{1c}$ are each as defined herein. In certain embodiments, $R^5$ is —NR$^{1a}$S(O)$_2$NR$^{1b}$R$^{1c}$, wherein R$^{1a}$, R$^{1b}$, and R$^{1c}$ are each as defined herein. In certain embodiments, $R^5$ is —SR$^{1a}$, wherein R$^{1a}$ is as defined herein. In certain embodiments, $R^5$ is —SR$^{1a}$, wherein R$^{1a}$ is C$_{1-6}$ alkyl, optionally substituted with one or more substituents Q. In certain embodiments, $R^5$ is —SR$^{1a}$, wherein R$^{1a}$ is C$_{1-6}$ alkyl, optionally substituted with one, two, or three halo. In certain embodiments, $R^5$ is —S(O)R$^{1a}$, wherein R$^{1a}$ is as defined herein. In certain embodiments, $R^5$ is —S(O)$_2$R$^{1a}$, wherein R$^{1a}$ is as defined herein. In certain embodiments, R is —S(O)NR$^{1b}$R$^{1c}$, wherein R$^{1b}$ and R$^{1c}$ are each as defined herein. In certain embodiments, $R^5$ is —S(O)$_2$NR$^{1b}$R$^{1c}$, wherein R$^{1b}$ and R$^{1c}$ are each as defined herein.

In certain embodiments, two of R$^1$, R$^2$, R$^3$, R$^4$, and R$^5$ are halo or C$_{1-6}$ alkyl optionally substituted with one or more substituents Q. In certain embodiments, two of R$^1$, R$^2$, R$^3$, R$^4$, and R$^5$ are halo or C$_{1-6}$ alkyl optionally substituted with one or more substituents Q, and the remaining three are hydrogen or deuterium. In certain embodiments, two of R$^1$, R$^2$, R$^3$, R$^4$, and R$^5$ are halo or C$_{1-6}$ alkyl optionally substituted with one or more substituents Q, and the remaining three are deuterium. In certain embodiments, two of R$^1$, R$^2$, R$^3$, R$^4$, and R$^5$ are chloro, methyl, —CH$_2$D, —CHD$_2$, or —CD$_3$. In certain embodiments, two of R$^1$, R$^2$, R$^3$, R$^4$, and R$^5$ are chloro, methyl, —CH$_2$D, —CHD$_2$, or —CD$_3$, and the remaining three are hydrogen or deuterium. In certain embodiments, two of R$^1$, R$^2$, R$^3$, R$^4$, and R$^5$ are chloro, methyl, —CH$_2$D, —CHD$_2$, or —CD$_3$, and the remaining three are deuterium.

In certain embodiments, R$^1$, R$^3$, and R$^5$ are hydrogen or deuterium, and R$^2$ and R$^4$ are halo or C$_{1-6}$ alkyl optionally substituted with one or more substituents Q. In certain embodiments, R$^1$, R$^3$, and R$^5$ are deuterium, and R$^2$ and R$^4$ are halo or C$_{1-6}$ alkyl optionally substituted with one or more substituents Q. In certain embodiments, R$^1$, R$^3$, and R$^5$ are hydrogen or deuterium, and R$^2$ and R$^4$ are chloro, methyl, —CH$_2$D, —CHD$_2$, or —CD$_3$. In certain embodiments, R$^1$, R$^3$, and R$^5$ are deuterium, and R$^2$ and R$^4$ are chloro, methyl, —CH$_2$D, —CHD$_2$, or —CD$_3$. In certain embodiments, R$^1$, R$^3$, and R$^5$ are hydrogen or deuterium, and R$^2$ and R$^4$ are chloro. In certain embodiments, R$^1$, R$^3$, and R$^5$ are deuterium, and R$^2$ and R$^4$ are chloro. In certain embodiments, R$^1$, R$^3$, and R$^5$ are hydrogen or deuterium, and R$^2$ and R$^4$ are methyl, —CH$_2$D, —CHD$_2$, or —CD$_3$. In certain embodiments, R$^1$, R$^3$, and R$^5$ are deuterium, and R$^2$ and R$^4$ are methyl, —CH$_2$D, —CHD$_2$, or —CD$_3$.

In certain embodiments, R$^2$, R$^3$, and R$^5$ are hydrogen or deuterium, and R$^1$ and R$^4$ are halo or C$_{1-6}$ alkyl optionally substituted with one or more substituents Q. In certain embodiments, R$^2$, R$^3$, and R$^5$ are deuterium, and R$^1$ and R$^4$ are halo or C$_{1-6}$ alkyl optionally substituted with one or more substituents Q. In certain embodiments, R$^2$, R$^3$, and R$^5$ are hydrogen or deuterium, and R$^1$ and R$^4$ are chloro, methyl, —CH$_2$D, —CHD$_2$, or —CD$_3$. In certain embodiments, R$^2$, R$^3$, and R$^5$ are deuterium, and R$^1$ and R$^4$ are chloro, methyl, —CH$_2$D, —CHD$_2$, or —CD$_3$. In certain embodiments, R$^2$, R$^3$, and R$^5$ are hydrogen or deuterium, and R$^1$ and R$^4$ are chloro. In certain embodiments, R$^2$, R$^3$, and R$^5$ are deuterium, and R$^1$ and R$^4$ are chloro. In certain embodiments, R$^2$, R$^3$, and R$^5$ are hydrogen or deuterium, and R$^1$ and R$^4$ are methyl, —CH$_2$D, —CHD$_2$, or —CD$_3$. In certain embodiments, R$^2$, R$^3$, and R$^5$ are deuterium, and R$^1$ and R$^4$ are methyl, —CH$_2$D, —CHD$_2$, or —CD$_3$.

In certain embodiments, R$^6$ is hydrogen. In certain embodiments, R$^6$ is deuterium.

In certain embodiments, R$^7$ is hydrogen. In certain embodiments, R$^7$ is deuterium.

In certain embodiments, R$^8$ is hydrogen. In certain embodiments, R$^8$ is deuterium. In certain embodiments, R$^8$ is halo. In certain embodiments, R$^8$ is fluoro, chloro, bromo, or iodo. In certain embodiments, R$^8$ is fluoro. In certain embodiments, R$^8$ is chloro. In certain embodiments, R$^8$ is cyano. In certain embodiments, R$^8$ is —$^{12}$CN. In certain embodiments, R$^8$ is —$^{13}$CN. In certain embodiments, R$^8$ is —$^{14}$CN. In certain embodiments, R is nitro. In certain embodiments, R$^8$ is guanidine. In certain embodiments, R$^8$ is C$_{1-6}$ alkyl, optionally substituted with one or more substituents Q. In certain embodiments, R$^8$ is C$_{1-6}$ alkyl, optionally substituted with one, two, or three halo. In certain embodiments, R$^8$ is methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, R$^8$ is methyl, —CH$_2$D, —CHD$_2$, or —CD$_3$. In certain embodiments, R$^8$ is C$_{2-6}$ alkenyl, optionally substituted with one or more substituents Q. In certain embodiments, R$^8$ is C$_{2-6}$ alkynyl, optionally substituted with one or more substituents Q. In certain embodiments, R$^8$ is C$_{3-7}$ cycloalkyl, optionally substituted with one or more substituents Q. In certain embodiments, R$^8$ is C$_{6-14}$ aryl, optionally substituted with one or more substituents Q. In certain embodiments, R$^8$ is C$_{7-15}$ aralkyl, optionally substituted with one or more substituents Q. In certain embodiments, R$^8$ is heteroaryl, optionally substituted with one or more substituents Q. In certain embodiments, R$^8$ is heterocyclyl, optionally substituted with one or more substituents Q.

In certain embodiments, R$^8$ is —C(O)R$^{1a}$, wherein R$^{1a}$ is as defined herein. In certain embodiments, R$^8$ is —C(O)OR$^{1a}$, wherein R$^{1a}$ is as defined herein. In certain embodiments, R$^8$ is —C(O)NR$^{1b}$R$^{1c}$, wherein R$^{1b}$ and R$^{1c}$ are each as defined herein. In certain embodiments, R$^8$ is —C(NR$^{1a}$)NR$^{1b}$R$^{1c}$, wherein R$^{1a}$, R$^{1b}$, and R$^{1c}$ are each as defined herein. In certain embodiments, R$^8$ is —OR$^{1a}$, wherein R$^{1a}$ is as defined herein. In certain embodiments, R$^8$ is —OR$^{1a}$, wherein R$^{1a}$ is C$_{1-6}$ alkyl, optionally substituted with one or more substituents Q. In certain embodiments, R$^8$ is —OR$^{1a}$, wherein R$^{1a}$ is C$_{1-6}$ alkyl, optionally substituted with one, two, or three halo. In certain embodiments, R$^8$ is —OC(O)R$^{1a}$, wherein R$^{1a}$ is as defined herein. In certain embodiments, R$^8$ is —OC(O)OR$^{1a}$, wherein R$^{1a}$ is as defined herein. In certain embodiments, R$^8$ is —OC(O)NR$^{1b}$R$^{1c}$, wherein R$^{1b}$ and R$^{1c}$ are each as defined herein. In certain embodiments, R$^8$ is —OC(=NR$^{1a}$)NR$^{1b}$R$^{1c}$, wherein R$^{1a}$, R$^{1b}$, and R$^{1c}$ are each as defined herein. In certain embodiments, R$^8$ is —OS(O)R$^{1a}$, wherein R$^{1a}$ is as defined herein. In certain embodiments, R$^8$ is —OS(O)$_2$R$^{1a}$, wherein R$^{1a}$ is as defined herein. In certain embodiments, R$^8$ is —OS(O)

$NR^{1b}R^{1c}$, wherein $R^{1b}$ and $R^{1c}$ are each as defined herein. In certain embodiments, $R^8$ is $-OS(O)_2NR^{1b}R^{1c}$, wherein $R^{1b}$ and $R^{1c}$ are each as defined herein. In certain embodiments, $R^8$ is $-NR^{1b}R^{1c}$, wherein $R^{1b}$ and $R^{1c}$ are each as defined herein. In certain embodiments, $R^8$ is $-NR^{1a}C(O)R^{1d}$, wherein $R^{1a}$ and $R^{1d}$ are each as defined herein. In certain embodiments, $R^8$ is $-NR^aC(O)OR^{1d}$, wherein $R^{1a}$ and $R^{1d}$ are each as defined herein. In certain embodiments, $R^8$ is $-NR^{1a}C(O)NR^{1b}R^{1c}$, wherein $R^{1a}$, $R^{1b}$, and $R^{1c}$ are each as defined herein. In certain embodiments, $R^8$ is $-NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^8$ is $-NR^{1a}S(O)R^d$, wherein $R^{1a}$ and $R^{1d}$ are each as defined herein. In certain embodiments, $R^8$ is $-NR^{1a}S(O)_2R^{1d}$, wherein $R^{1a}$ and $R^{1d}$ are each as defined herein. In certain embodiments, $R^8$ is $-NR^{1a}S(O)NR^{1b}R^{1c}$, wherein $R^{1a}$, $R^{1b}$, and $R^{1c}$ are each as defined herein. In certain embodiments, $R^8$ is $-NR^{1a}S(O)_2NR^{1b}R^{1c}$, wherein $R^{1a}$, $R^{1b}$, and $R^{1c}$ are each as defined herein. In certain embodiments, $R^8$ is $-SR^{1a}$, wherein $R^{1a}$ is as defined herein. In certain embodiments, $R^8$ is $-SR^{1a}$, wherein $R^{1a}$ is $C_{1-6}$ alkyl, optionally substituted with one or more substituents Q. In certain embodiments, $R^8$ is $-SR^{1a}$, wherein $R^{1a}$ is $C_{1-6}$ alkyl, optionally substituted with one, two, or three halo. In certain embodiments, $R^8$ is $-S(O)R^{1a}$, wherein $R^{1a}$ is as defined herein. In certain embodiments, $R^8$ is $-S(O)_2R^{1a}$, wherein $R^{1a}$ is as defined herein. In certain embodiments, $R^8$ is $-S(O)NR^{1b}R^{1c}$, wherein $R^{1b}$ and $R^{1c}$ are each as defined herein. In certain embodiments, $R^8$ is $-S(O)_2NR^{1b}R^{1c}$, wherein $R^{1b}$ and $R^{1c}$ are each as defined herein.

In certain embodiments, $R^9$ is hydrogen. In certain embodiments, $R^9$ is deuterium.

In certain embodiments, at least one of $R^6$, $R^7$, and $R^9$ is deuterium. In certain embodiments, at least two of $R^6$, $R^7$, and $R^9$ are deuterium. In certain embodiments, $R^6$, $R^7$, and $R^9$ are deuterium.

In certain embodiments, $R^{10}$ is hydrogen. In certain embodiments, $R^{10}$ is $C_{1-6}$ alkyl, optionally substituted with one or more substituents Q. In certain embodiments, $R^{10}$ is methyl, $-CH_2D$, $-CHD_2$, or $-CD_3$. In certain embodiments, $R^{10}$ is $C_{2-6}$ alkenyl, optionally substituted with one or more substituents Q. In certain embodiments, $R^{10}$ is $C_{2-6}$ alkynyl, optionally substituted with one or more substituents Q. In certain embodiments, $R^{10}$ is $C_{3-7}$ cycloalkyl, optionally substituted with one or more substituents Q. In certain embodiments, $R^{10}$ is cyclopentyl. In certain embodiments, $R^{10}$ is $C_{6-14}$ aryl, optionally substituted with one or more substituents Q. In certain embodiments, $R^{10}$ is $C_{7-15}$ aralkyl, optionally substituted with one or more substituents Q. In certain embodiments, $R^{10}$ is heteroaryl, optionally substituted with one or more substituents Q. In certain embodiments, $R^{10}$ is heterocyclyl, optionally substituted with one or more substituents Q. In certain embodiments, $R^{10}$ is $-C(O)R^{1a}$, wherein $R^{1a}$ is as defined herein. In certain embodiments, $R^{10}$ is not $-C(O)H$. In certain embodiments, $R^{10}$ is $-C(O)OR^{1a}$, wherein $R^{1a}$ is as defined herein. In certain embodiments, $R^{10}$ is $-C(O)OR^{1a}$, wherein $R^{1a}$ is as defined herein, but $R^{1a}$ is not -t-butyl, 9-fluorenylmethyl, or benzyl. In certain embodiments, $R^{10}$ is not $-C(O)O-C_{1-6}$ alkyl. In certain embodiments, $R^{10}$ is $-C(O)O-C_{1-6}$ alkyl, but not $-C(O)O$-t-butyl. In certain embodiments, $R^{10}$ is $-C(O)O$-ethyl, optionally substituted with one or more substituents Q. In certain embodiments, $R^{10}$ is $-C(O)NR^{1b}R^{1c}$, wherein $R^{1b}$ and $R^{1c}$ are each as defined herein. In certain embodiments, $R^{10}$ is $-C(NR^{1a})NR^{1b}R^{1c}$, wherein $R^{1a}$, $R^{1b}$, and $R^{1c}$ are each as defined herein. In certain embodiments, $R^{10}$ is $-S(O)R^{1a}$, wherein $R^{1a}$ is as defined herein. In certain embodiments, $R^{10}$ is $-S(O)_2R^{1a}$, wherein $R^{1a}$ is as defined herein. In certain embodiments, $R^{10}$ is $-S(O)NR^{1b}R^{1c}$, wherein $R^{1b}$ and $R^{1c}$ are each as defined herein. In certain embodiments, $R^{10}$ is $-S(O)_2NR^{1b}R^{1c}$, wherein $R^{1b}$ and $R^{1c}$ are each as defined herein.

In certain embodiments, $R^{11}$ is hydrogen. In certain embodiments, $R^{11}$ is deuterium. In certain embodiments, $R^{11}$ is halo. In certain embodiments, $R^{11}$ is fluoro, chloro, bromo, or iodo. In certain embodiments, $R^{11}$ is fluoro. In certain embodiments, $R^{11}$ is chloro. In certain embodiments, $R^{11}$ is cyano. In certain embodiments, $R^{11}$ is $-^{13}CN$. In certain embodiments, $R^{11}$ is nitro. In certain embodiments, $R^{11}$ is oxo. In certain embodiments, $R^{11}$ is guanidine. In certain embodiments, $R^{11}$ is $C_{1-6}$ alkyl, optionally substituted with one or more substituents Q. In certain embodiments, $R^{11}$ is $C_{1-6}$ alkyl, optionally substituted with one, two, or three halo. In certain embodiments, $R^{11}$ is methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^{11}$ is methyl, $-CH_2D$, $-CHD_2$, or $-CD_3$. In certain embodiments, $R^{11}$ is $C_{2-6}$ alkenyl, optionally substituted with one or more substituents Q. In certain embodiments, $R^{11}$ is $C_{2-6}$ alkynyl, optionally substituted with one or more substituents Q. In certain embodiments, $R^{11}$ is $C_{3-7}$ cycloalkyl, optionally substituted with one or more substituents Q. In certain embodiments, $R^{11}$ is $C_{6-14}$ aryl, optionally substituted with one or more substituents Q. In certain embodiments, $R^{11}$ is $C_{7-15}$ aralkyl, optionally substituted with one or more substituents Q. In certain embodiments, $R^{11}$ is heteroaryl, optionally substituted with one or more substituents Q. In certain embodiments, $R^{11}$ is heterocyclyl, optionally substituted with one or more substituents Q.

In certain embodiments, $R^{11}$ is $-C(O)R^{1a}$, wherein $R^{1a}$ is as defined herein. In certain embodiments, $R^{11}$ is $-C(O)OR^{1a}$, wherein $R^{1a}$ is as defined herein. In certain embodiments, $R^{11}$ is $-C(O)NR^{1b}R^{1c}$, wherein $R^{1b}$ and $R^{1c}$ are each as defined herein. In certain embodiments, $R^{11}$ is $-C(NR^{1a})NR^{1b}R^{1c}$, wherein $R^{1a}$, $R^{1b}$, and $R^{1c}$ are each as defined herein. In certain embodiments, $R^{11}$ is $-OR^{1a}$, wherein $R^{1a}$ is as defined herein. In certain embodiments, $R^{11}$ is $-OR^{1a}$, wherein $R^{1a}$ is $C_{1-6}$ alkyl, optionally substituted with one or more substituents Q. In certain embodiments, $R^{11}$ is $-OR^{1a}$, wherein $R^{1a}$ is $C_{1-6}$ alkyl, optionally substituted with one, two, or three halo. In certain embodiments, $R^{11}$ is $-OC(O)R^{1a}$, wherein $R^{1a}$ is as defined herein. In certain embodiments, $R^{11}$ is $-OC(O)OR^{1a}$, wherein $R^{1a}$ is as defined herein. In certain embodiments, $R^{11}$ is $-OC(O)NR^{1b}R^{1c}$, wherein $R^{1b}$ and $R^{1c}$ are each as defined herein. In certain embodiments, $R^{11}$ is $-OC(=NR^{1a})NR^{1b}R^{1c}$, wherein $R^{1a}$, $R^{1b}$, and $R^{1c}$ are each as defined herein. In certain embodiments, $R^{11}$ is $-OS(O)R^{1a}$, wherein $R^{1a}$ is as defined herein. In certain embodiments, $R^{11}$ is $-OS(O)_2R^{1a}$, wherein $R^{1a}$ is as defined herein. In certain embodiments, $R^{11}$ is $-OS(O)NR^{1b}R^{1c}$, wherein $R^{1b}$ and $R^{1c}$ are each as defined herein. In certain embodiments, $R^{11}$ is $-OS(O)_2NR^{1b}R^{1c}$, wherein $R^{1b}$ and $R^{1c}$ are each as defined herein. In certain embodiments, $R^{11}$ is $-NR^{1b}R^{1c}$, wherein $R^{1b}$ and $R^{1c}$ are each as defined herein. In certain embodiments, $R^{11}$ is $-NR^{1a}C(O)R^{1d}$, wherein R and $R^{1d}$ are each as defined herein. In certain embodiments, $R^{11}$ is $-NR^{1a}C(O)OR^{1d}$, wherein $R^{1a}$ and $R^{1d}$ are each as defined herein. In certain embodiments, $R^{11}$ is $-NR^{1a}C(O)NR^{1b}R^{1c}$, wherein $R^{1a}$, $R^{1b}$, and $R^{1c}$ are each as defined herein. In certain embodiments, $R^{11}$ is $-NR^{1a}C(=NR^d)NR^{1b}R^{1c}$, wherein $R^{1a}$, $R^{1b}$, $R^{1c}$, and $R^{1d}$ are each as defined herein. In certain embodiments, $R^{11}$ is $-NR^{1a}S$ (O)R$^{1d}$, wherein R$^{1a}$ and R$^{1d}$ are each as defined herein. In certain embodiments, R$^{11}$ is —NR$^{1a}$S(O)$_2$R$^{1d}$, wherein R$^{1a}$ and R$^{1d}$ are each as defined herein. In certain embodiments, R$^{11}$ is —NR$^{1a}$S(O)NR$^{1b}$R$^{1c}$, wherein R$^{1a}$, R$^{1b}$, and R$^{1c}$ are each as defined herein. In certain embodiments, R$^{11}$ is —NR$^{1a}$S(O)$_2$NR$^{1b}$R$^{1c}$, wherein R$^{1a}$, R$^{1b}$, and R$^{1c}$ are each as defined herein. In certain embodiments, R$^{11}$ is —SR$^{1a}$, wherein R$^{1a}$ is as defined herein. In certain embodiments, R$^{11}$ is —SR$^{1a}$, wherein R$^{1a}$ is C$_{1-6}$ alkyl, optionally substituted with one or more substituents Q. In certain embodiments, R$^{11}$ is —SR$^{1a}$, wherein R$^{1a}$ is C$_{1-6}$ alkyl, optionally substituted with one, two, or three halo. In certain embodiments, R$^{11}$ is —S(O)R$^a$, wherein R$^{1a}$ is as defined herein. In certain embodiments, R$^{11}$ is —S(O)$_2$R$^{1a}$, wherein R$^{1a}$ is as defined herein. In certain embodiments, R$^{11}$ is —S(O)NR$^{1b}$R$^{1c}$, wherein R$^{1b}$ and R$^{1c}$ are each as defined herein. In certain embodiments, R$^{11}$ is —S(O)$_2$NR$^{1b}$R$^{1c}$, wherein R$^{1b}$ and R$^{1c}$ are each as defined herein.

In certain embodiments, X is O. In certain embodiments, X is $^{15}$O. In certain embodiments, X is $^{16}$O. In certain embodiments, X is $^{17}$O. In certain embodiments, X is $^{18}$O. In certain embodiments, X is $^{18}$O. In certain embodiments, X is S. In certain embodiments, X is $^{32}$S. In certain embodiments, X is $^{33}$S. In certain embodiments, X is $^{34}$S. In certain embodiments, X is $^{35}$S. In certain embodiments, X is $^{36}$S.

In certain embodiments, m is 0. In certain embodiments, m is 1. In certain embodiments, m is 2. In certain embodiments, m is 3.

In certain embodiments, n is 1. In certain embodiments, n is 2. In certain embodiments, n is 3.

In certain embodiments, m is 1 and n is 1. In certain embodiments, m is 1 and n is 2.

In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8. In certain embodiments, p is 9. In certain embodiments, p is 10. In certain embodiments, p is 11. In certain embodiments, p is 12. In certain embodiments, p is 13. In certain embodiments, p is 14.

In certain embodiments, R$^{1a}$ is hydrogen. In certain embodiments, R$^{1a}$ is deuterium. In certain embodiments, R$^{1a}$ is C$_{1-6}$ alkyl, optionally substituted with one or more substituents Q. In certain embodiments, R$^{1a}$ is methyl, ethyl, propyl (e.g., n-propyl or isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, R$^{1a}$ is methyl, ethyl, isopropyl, isobutyl, t-butyl, 1,1-dimethylpropyl, or 2,2-dimethylpropyl. In certain embodiments, R$^{1a}$ is C$_{2-6}$ alkenyl, optionally substituted with one or more substituents Q. In certain embodiments, R$^{1a}$ is C$_{2-6}$ alkynyl, optionally substituted with one or more substituents Q. In certain embodiments, R$^{1a}$ is C$_{3-7}$ cycloalkyl, optionally substituted with one or more substituents Q. In certain embodiments, R$^{1a}$ is C$_{3-7}$ cycloalkyl, optionally substituted with one or two C$_{1-6}$ alkyl. In certain embodiments, R$^{1a}$ is C$_{3-7}$ cycloalkyl, optionally substituted with two methyl groups. In certain embodiments, R$^{1a}$ is cyclobutyl, cyclopentyl, cyclohexyl, or dimethylbicyclo[2.2.1]heptyl (e.g., 7,7-dimethylbicyclo[2.2.1]-heptyl). In certain embodiments, R$^{1a}$ is cyclobutyl, cyclopentyl, cyclohexyl, or (1S,2S,4R)-7,7-dimethylbicyclo[2.2.1]-heptyl. In certain embodiments, R$^{1a}$ is C$_{6-14}$ aryl, optionally substituted with one or more substituents Q. In certain embodiments, R$^{1a}$ is C$_{6-14}$ aryl, optionally substituted with one or more halo or C$_{1-6}$ alkyl, wherein the alkyl is optionally substituted with one, two, or three halo. In certain embodiments, R$^{1a}$ is C$_{6-14}$ aryl, optionally substituted with fluoro, chloro, methyl, trifluoromethyl, or ethyl. In certain embodiments, R$^{1a}$ is phenyl, fluorophenyl (e.g., 2-fluorophenyl, 3-fluorophenyl, or 4-fluorophenyl), chlorophenyl (e.g., 2-chlorophenyl, 3-chlorophenyl, or 4-chlorophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), or ethylphenyl (e.g., 2-ethylphenyl, 3-ethylphenyl, or 4-ethylphenyl). In certain embodiments, R$^{1a}$ is phenyl, 3-fluorophenyl, 3-methylphenyl, 4-chlorophenyl, 4-methylphenyl, 4-trifluoromethylphenyl, or 4-ethylphenyl. In certain embodiments, R$^{1a}$ is heteroaryl, optionally substituted with one or more substituents Q. In certain embodiments, R$^{1a}$ is heterocyclyl, optionally substituted with one or more substituents Q.

In certain embodiments, R$^{1b}$ is hydrogen. In certain embodiments, R$^{1b}$ is deuterium. In certain embodiments, R$^{1b}$ is C$_{1-6}$ alkyl, optionally substituted with one or more substituents Q. In certain embodiments, R$^{1b}$ is C$_{2-6}$ alkenyl, optionally substituted with one or more substituents Q. In certain embodiments, R$^{1b}$ is C$_{2-6}$ alkynyl, optionally substituted with one or more substituents Q. In certain embodiments, R$^{1b}$ is C$_{3-7}$ cycloalkyl, optionally substituted with one or more substituents Q. In certain embodiments, R$^{1b}$ is C$_{6-14}$ aryl, optionally substituted with one or more substituents Q. In certain embodiments, R$^{1b}$ is heteroaryl, optionally substituted with one or more substituents Q. In certain embodiments, R$^{1b}$ is heterocyclyl, optionally substituted with one or more substituents Q.

In certain embodiments, R$^{1c}$ is hydrogen. In certain embodiments, R$^{1c}$ is deuterium. In certain embodiments, R$^{1c}$ is C$_{1-6}$ alkyl, optionally substituted with one or more substituents Q. In certain embodiments, R$^{1c}$ is methyl, ethyl, propyl (e.g., n-propyl or isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, R$^{1c}$ is methyl, ethyl, isopropyl, isobutyl, t-butyl, 1,1-dimethylpropyl, or 2,2-dimethylpropyl. In certain embodiments, R$^{1c}$ is C$_{2-6}$ alkenyl, optionally substituted with one or more substituents Q. In certain embodiments, R$^{1c}$ is C$_{2-6}$ alkynyl, optionally substituted with one or more substituents Q. In certain embodiments, R$^{1c}$ is C$_{3-7}$ cycloalkyl, optionally substituted with one or more substituents Q. In certain embodiments, R$^{1c}$ is C$_{3-7}$ cycloalkyl, optionally substituted with one or two C$_{1-6}$ alkyl. In certain embodiments, R$^{1c}$ is C$_{3-7}$ cycloalkyl, optionally substituted with two methyl groups. In certain embodiments, R$^{1c}$ is cyclobutyl, cyclopentyl, cyclohexyl, or dimethylbicyclo[2.2.1]heptyl (e.g., 7,7-dimethylbicyclo[2.2.1]-heptyl). In certain embodiments, R$^{1c}$ is cyclobutyl, cyclopentyl, cyclohexyl, or (1S,2S,4R)-7,7-dimethylbicyclo[2.2.1]-heptyl. In certain embodiments, R$^{1c}$ is C$_{6-14}$ aryl, optionally substituted with one or more substituents Q. In certain embodiments, R$^{1c}$ is C$_{6-14}$ aryl, optionally substituted with one or more halo or C$_{1-6}$ alkyl, wherein the alkyl is optionally substituted with one, two, or three halo. In certain embodiments, R$^{1c}$ is C$_{6-14}$ aryl, optionally substituted with fluoro, chloro, methyl, trifluoromethyl, or ethyl. In certain embodiments, R$^{1c}$ is phenyl, fluorophenyl (e.g., 2-fluorophenyl, 3-fluorophenyl, or 4-fluorophenyl), chlorophenyl (e.g., 2-chlorophenyl, 3-chlorophenyl, or 4-chlorophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), or ethylphenyl (e.g., 2-ethylphenyl, 3-ethylphenyl, or 4-ethylphenyl). In certain embodiments, $R^{1c}$ is phenyl, 3-fluorophenyl, 3-methylphenyl, 4-chlorophenyl, 4-methylphenyl, 4-trifluoromethylphenyl, or 4-ethylphenyl. In certain embodiments, $R^{1c}$ is heteroaryl, optionally substituted with one or more substituents Q. In certain embodiments, $R^{1c}$ is heterocyclyl.

In certain embodiments, $R^{1b}$ and $R^{1c}$ together with the N atom to which they are attached independently form heteroaryl, optionally substituted with one or more substituents Q. In certain embodiments, $R^{1b}$ and $R^{1c}$ together with the N atom to which they are attached independently form heterocyclyl, optionally substituted with one or more substituents Q.

In certain embodiments, $R^{1d}$ is hydrogen. In certain embodiments, $R^{1d}$ is deuterium. In certain embodiments, $R^{1d}$ is $C_{1-6}$ alkyl, optionally substituted with one or more substituents Q. In certain embodiments, $R^{1d}$ is $C_{2-6}$ alkenyl, optionally substituted with one or more substituents Q. In certain embodiments, $R^{1d}$ is $C_{2-6}$ alkynyl, optionally substituted with one or more substituents Q. In certain embodiments, $R^{1d}$ is $C_{3-7}$ cycloalkyl, optionally substituted with one or more substituents Q. In certain embodiments, $R^{1d}$ is $C_{6-14}$ aryl, optionally substituted with one or more substituents Q. In certain embodiments, $R^{1d}$ is heteroaryl, optionally substituted with one or more substituents Q. In certain embodiments, $R^{1d}$ is heterocyclyl, optionally substituted with one or more substituents Q.

In certain embodiments, $R^{11a}$ is hydrogen. In certain embodiments, $R^{11a}$ is deuterium.

In certain embodiments, $R^{11b}$ is hydrogen. In certain embodiments, $R^{11b}$ is deuterium.

In certain embodiments, $R^{11c}$ is hydrogen. In certain embodiments, $R^{11c}$ is deuterium.

In certain embodiments, $R^{11d}$ is hydrogen. In certain embodiments, $R^{11d}$ is deuterium.

In certain embodiments, $R^{11e}$ is hydrogen. In certain embodiments, $R^{11e}$ is deuterium.

In certain embodiments, $R^{11f}$ is hydrogen. In certain embodiments, $R^{11f}$ is deuterium.

In certain embodiments, $R^{11a}$ and $R^{11b}$ are deuterium. In certain embodiments, $R^{11c}$ and $R^{11d}$ are deuterium. In certain embodiments, $R^{11e}$ and $R^{11f}$ are deuterium.

In certain embodiments, at least one of $R^{11a}$, $R^{11b}$, $R^{11c}$, $R^{11d}$, $R^{11e}$, and $R^{11f}$ is deuterium. In certain embodiments, at least two of $R^{11a}$, $R^{11b}$, $R^{11c}$, $R^{11d}$, $R^{11e}$, and $R^{11f}$ are deuterium. In certain embodiments, at least three of $R^{11a}$, $R^{11b}$, $R^{11c}$, $R^{11d}$, $R^{11e}$, and $R^{11f}$ are deuterium. In certain embodiments, at least four of $R^{11a}$, $R^{11b}$, $R^{11c}$, $R^{11d}$, $R^{11e}$, and $R^{11f}$ are deuterium. In certain embodiments, at least five of $R^{11a}$, $R^{11b}$, $R^{11c}$, $R^{11d}$, $R^{11e}$, and $R^{11f}$ are deuterium. In certain embodiments, at least six of $R^{11a}$, $R^{11b}$, $R^{11c}$, $R^{11d}$, $R^{11e}$, and $R^{11f}$ are deuterium. In certain embodiments, at least seven of $R^{11a}$, $R^{11b}$, $R^{11c}$, $R^{11d}$, $R^{11e}$, and $R^{11f}$ are deuterium. In certain embodiments, $R^{11a}$, $R^{11b}$, $R^{11c}$, $R^{11d}$, $R^{11e}$, and $R^{11f}$ are deuterium.

In certain embodiments, a compound provided herein is deuterium-enriched.

In certain embodiments, a compound provided herein is carbon-13 enriched. In certain embodiments, a compound provided herein is carbon-14 enriched. In certain embodiments, a compound provided herein contains one or more less prevalent isotopes for other elements, including, but not limited to, $^{15}N$ for nitrogen; $^{17}O$ or $^{18}O$ for oxygen, and $^{33}S$, $^{34}S$, or $^{36}S$ for sulfur.

In one embodiment, provided herein is a compound selected from:

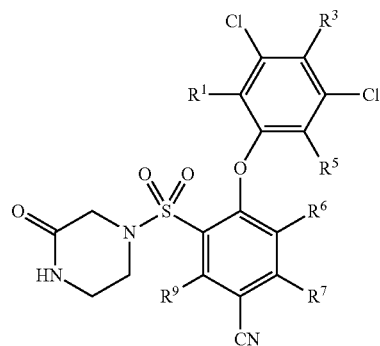

| Cmpd. | $R^1$ | $R^3$ | $R^5$ | $R^6$ | $R^7$ | $R^9$ |
|---|---|---|---|---|---|---|
| 1 | D | H | H | H | H | H |
| 2 | H | D | H | H | H | H |
| 3 | H | H | D | H | H | H |
| 4 | H | H | H | D | H | H |
| 5 | H | H | H | H | D | H |
| 6 | H | H | H | H | H | D |
| 7 | D | D | H | H | H | H |
| 8 | D | H | D | H | H | H |
| 9 | D | H | H | D | H | H |
| 10 | D | H | H | H | D | H |
| 11 | D | H | H | H | H | D |
| 12 | H | D | D | H | H | H |
| 13 | H | D | H | D | H | H |
| 14 | H | D | H | H | D | H |
| 15 | H | D | H | H | H | D |
| 16 | H | H | D | D | H | H |
| 17 | H | H | D | H | D | H |
| 18 | H | H | D | H | H | H |
| 19 | H | H | H | D | D | H |
| 20 | H | H | H | D | H | D |
| 21 | H | H | H | H | D | D |
| 22 | D | D | D | H | H | H |
| 23 | D | D | D | D | H | H |
| 24 | D | D | D | H | D | H |
| 25 | D | D | D | H | H | D |
| 26 | D | D | D | D | D | H |
| 27 | D | D | D | D | H | D |
| 28 | D | D | D | H | D | D |
| 29 | H | H | H | D | D | D |
| 30 | D | H | H | D | D | D |
| 31 | H | D | H | D | D | D |
| 32 | H | H | D | D | D | D |
| 33 | D | D | H | D | D | D |
| 34 | D | H | D | D | D | D |
| 35 | H | D | D | D | D | D |
| 36 | D | D | D | D | D | D | and pharmaceutically acceptable salts, solvates, hydrates, and prodrugs thereof.

In another embodiment, provided herein is a compound selected from:

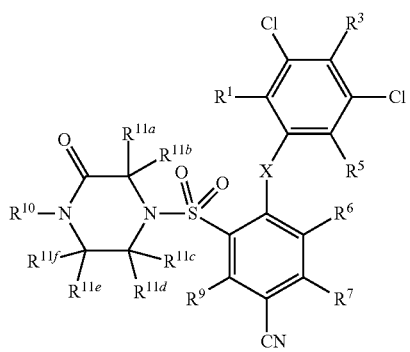

| Cmpd. | $R^1$ | $R^3$ | $R^5$ | $R^6$ | $R^7$ | $R^9$ | $R^{11a}$ | $R^{11b}$ | $R^{11c}$ | $R^{11d}$ | $R^{11e}$ | $R^{11f}$ |
|---|---|---|---|---|---|---|---|---|---|---|---|---|
| 51 | H | H | H | H | H | H | D | D | H | H | H | H |
| 52 | H | H | H | H | H | H | H | H | D | D | H | H |
| 53 | H | H | H | H | H | H | H | H | H | H | D | D |
| 54 | H | H | H | H | H | H | D | D | D | D | H | H |
| 55 | H | H | H | H | H | H | D | D | H | H | D | D |
| 56 | H | H | H | H | H | H | H | H | D | D | D | D |
| 57 | H | H | H | H | H | H | D | D | D | D | D | D |
| 58 | D | D | D | H | H | H | D | D | H | H | H | H |
| 59 | D | D | D | H | H | H | H | H | D | D | H | H |
| 60 | D | D | D | H | H | H | H | H | H | H | D | D |
| 61 | D | D | D | H | H | H | D | D | D | D | H | H |
| 62 | D | D | D | H | H | H | D | D | H | H | D | D |
| 63 | D | D | D | H | H | H | H | H | D | D | D | D |
| 64 | D | D | D | H | H | H | D | D | D | D | D | D |
| 65 | H | H | H | D | D | D | D | D | H | H | H | H |
| 66 | H | H | H | D | D | D | H | H | D | D | H | H |
| 67 | H | H | H | D | D | D | H | H | H | H | D | D |
| 68 | H | H | H | D | D | D | D | D | D | D | H | H |
| 69 | H | H | H | D | D | D | D | D | H | H | D | D |
| 70 | H | H | H | D | D | D | H | H | D | D | D | D |
| 71 | H | H | H | D | D | D | D | D | D | D | D | D |
| 72 | D | D | D | D | D | D | D | D | H | H | H | H |
| 73 | D | D | D | D | D | D | H | H | D | D | H | H |
| 74 | D | D | D | D | D | D | H | H | H | H | D | D |
| 75 | D | D | D | D | D | D | D | D | D | D | H | H |
| 76 | D | D | D | D | D | D | D | D | H | H | D | D |
| 77 | D | D | D | D | D | D | H | H | D | D | D | D |
| 78 | D | D | D | D | D | D | D | D | D | D | D | D | and pharmaceutically acceptable salts, solvates, hydrates, and prodrugs thereof.

In yet another embodiment, provided herein is 4-(3,5-dichloro-2,4,6-trideuteriumphenoxy)-3-(3-oxo-piperazine-1-sulfonyl)-2,5,6-trideuteriumbenzonitrile, or a pharmaceutically acceptable salt, solvate, hydrate, or prodrug thereof.

In certain embodiments, a compound provided herein has an isotopic enrichment factor of no less than about 5, no less than about 10, no less than about 20, no less than about 30, no less than about 40, no less than about 50, no less than about 60, no less than about 70, no less than about 80, no less than about 90, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when a compound at a given position is 100% enriched with the specified isotope. Thus, the maximum isotopic enrichment factors are different for different isotopes. The maximum isotopic enrichment factor is 6410 for deuterium and 90 for carbon-13.

In certain embodiments, a compound provided herein is deuterium enriched. In certain embodiments, a compound provided herein has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, e.g., mass spectrometry or nuclear magnetic resonance spectroscopy.

In certain embodiments, a compound provided herein is carbon-13 enriched. In certain embodiments, the compound provided herein have a carbon-13 enrichment factor of no less than about 1.8 (about 2% carbon-13 enrichment), no less than about 4.5 (about 5% carbon-13 enrichment), no less than about 9 (about 10% carbon-13 enrichment), no less than about 18 (about 20% carbon-13 enrichment), no less than about 45 (about 50% carbon-13 enrichment), no less than about 68 (about 75% carbon-13 enrichment), no less than about 72 (about 80% carbon-13 enrichment), no less than about 77 (about 85% carbon-13 enrichment), no less than about 81 (about 90% carbon-13 enrichment), no less than about 86 (about 95% carbon-13 enrichment), no less than about 87 (about 97% carbon-13 enrichment), no less than about 88 (about 98% carbon-13 enrichment), no less than about 89 (about 99% carbon-13 enrichment), or no less than about 90 (about 99.5% carbon-13 enrichment). The carbon-13 enrichment can be determined using conventional analytical methods known to one of ordinary skill in the art, e.g., mass spectrometry or nuclear magnetic resonance spectroscopy.

In certain embodiments, at least one of the atoms of a compound provided herein, as specified as isotopically enriched, has isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of a compound provided herein, as specified as isotopically enriched, have isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In any events, the isotopic enrichment of each of the isotopically enriched atoms of a compound provided herein is no less than the natural abundance of the isotope specified.

In certain embodiments, at least one of the atoms of a compound provided herein, as specified as deuterium-enriched, has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of a compound provided herein, as specified as deuterium-enriched, have deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, at least one of the atoms of a compound provided herein, as specified as $^{13}$C-enriched, has carbon-13 enrichment of no less than about 2%, no less than about 5%, no less than about 10%, no less than about 20%, no less than about 50%, no less than about 70%, no less than about 80%, no less than about 90%, or no less than about 98%. In certain embodiments, the atoms of a compound provided herein, as specified as $^{13}$C-enriched, have carbon-13 enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, a compound provided herein is isolated or purified. In certain embodiments, a compound provided herein has a purity of at least about 50%, at least about 70%, at least about 80%, at least about 90%, at least about 95%, at least about 98%, at least about 99%, or at least about 99.5% by weight.

The compounds provided herein are intended to encompass all possible stereoisomers, unless a particular stereochemistry is specified. Where the compounds provided herein contain an alkenyl or alkenylene group, the compounds may exist as one or mixture of geometric cis/trans (or Z/E) isomers. Where structural isomers are interconvertible, the compounds may exist as a single tautomer or a mixture of tautomers. This can take the form of proton tautomerism in the compounds that contain, for example, an imino, keto, or oxime group; or so-called valence tautomerism in the compounds that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compounds provided herein contain an acidic or basic moiety, they each may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

In one embodiment, the compounds provided herein are a hydrochloride salt.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

A compound provided herein provided herein may also be provided as a prodrug, which is a functional derivative of the compound, for example, a compound of Formula I, and is readily convertible into the parent compound in vivo. Prodrugs are often useful because, in some situations, they may be easier to administer than their parent compound. They may, for instance, be bioavailable by oral administration whereas the parent compound is not. The prodrugs may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asghamejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Methods of Synthesis

The compounds provided herein can be prepared, isolated, or obtained by any method known to one of skill in the art. For an example, a compound of Formula I can be prepared according to the methods described in International Pat. App. Pub. Nos.: WO 2003/022277 and WO 2004/084898; and U.S. Pat. App. Pub. Nos.: US 2010/0273782, US 2010/0273785, US 2010/0273795, and US 2011/0218207; the disclosure of each of which is incorporated herein by reference in its entirety.

In one embodiment, an isotope is introduced into a compound provided herein by synthetic techniques that employ suitable isotopically enriched reagents, whereby isotopic enrichment is pre-determined. In another embodiment, an isotope is introduced into a compound provided herein by exchange techniques, wherein isotopic enrichment is determined by equilibrium conditions, which may be highly variable depending on the reaction conditions. In yet another embodiment, deuterium is introduced into a compound provided herein by direct deuteration.

In certain embodiments, deuterium is incorporated synthetically into one or more positions of a compound of Formula I, according to the synthetic procedures as shown in Scheme I, using appropriate deuterated starting materials or intermediates. In general, compound A1 reacts with compound A2 via a nucleophilic aromatic substitution reaction to form compound A3 with the release of hydrochloride. The nitro group of compound A3 is reduced to an amino group with a reducing reagent, e.g., sodium hydrosulfite or tin (II) chloride, to form analine A4, which is subsequently converted into sulfonyl chloride A5 via the Sandmeyer reaction. Compound A5 is then coupled with amine A6 to form a compound of Formula I.

In one embodiment, to introduce deuterium at one or more positions or groups of $R^1$, $R^2$, $R^3$, $R^4$, and $R^5$, compound A2 with the corresponding deuterium is coupled with compound A1 via a nucleophilic aromatic substitution reaction to form compound A3 with the release of hydrochloride. In another embodiment, to introduce deuterium at one or more positions or groups of $R^6$, $R^7$, $R^8$, and $R^9$, nitrobenzene A1 with the corresponding deuterium substitutions is coupled with compound A2 via a nucleophilic aromatic substitution reaction to form deuterated compound A3. In yet another embodiment, to introduce deuterium at one or more positions or groups of the $R^{11}$ groups, compound A6 with the corresponding deuterium is coupled with sulfonyl chloride A5 to form a deuterated compound of Formula I.

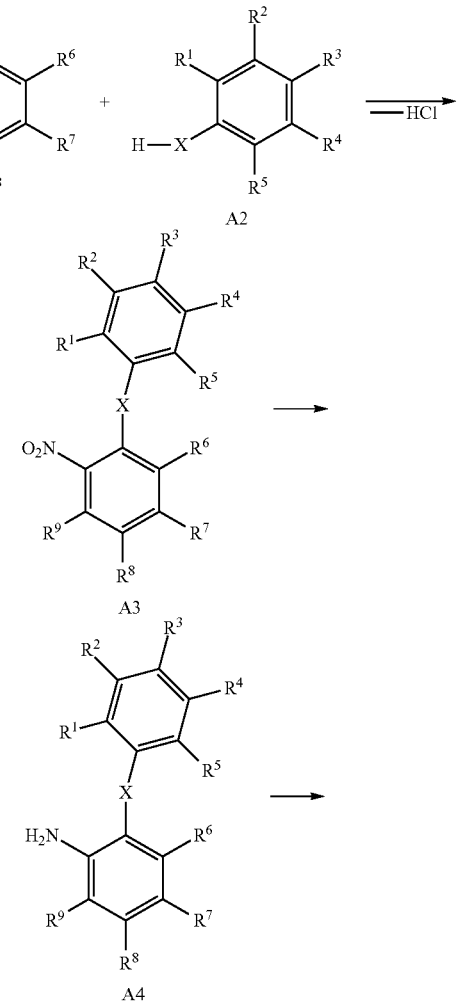

Scheme I

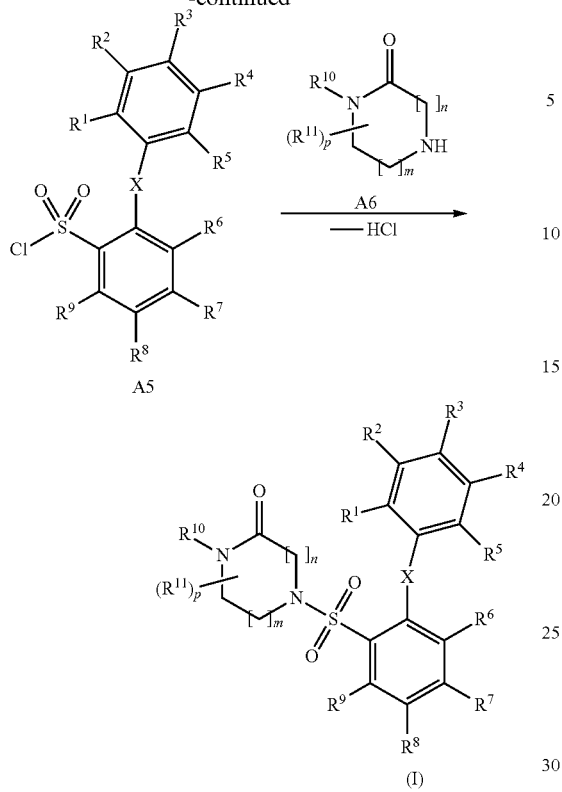

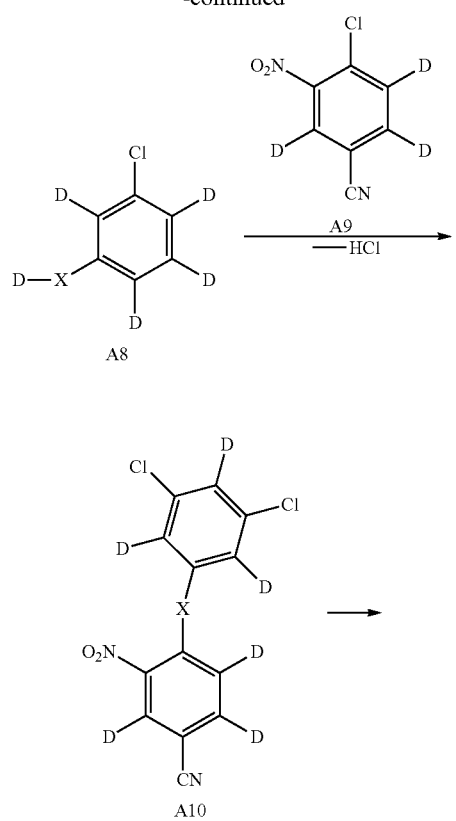

The deuterated starting materials and intermediates used herein are either commercially available, or can be prepared by methods known to one of skill in the art or by following procedures similar to those described herein in the Example section and routine modifications thereof.

In certain embodiments, deuterium is also incorporated to various positions of a compound of Formula I, which has an exchangeable proton, such as amine or amide N—H and hydroxyl O—H, via proton-deuterium equilibrium exchange.

Additional examples of the syntheses of deuterium-enriched and/or carbon-13 enriched compounds of Formula I are illustrated in Schemes II and III.

Pharmaceutical Compositions

Provided herein are pharmaceutical compositions comprising a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and a pharmaceutically acceptable excipient.

Scheme II

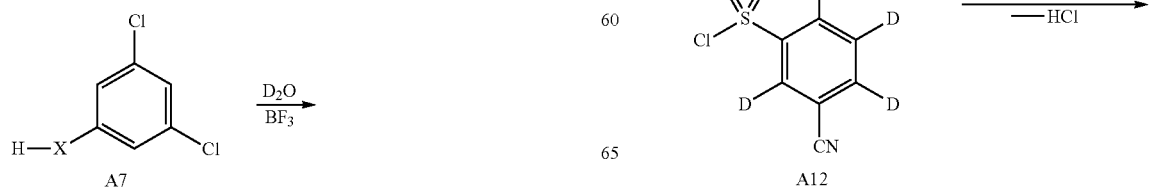

-continued

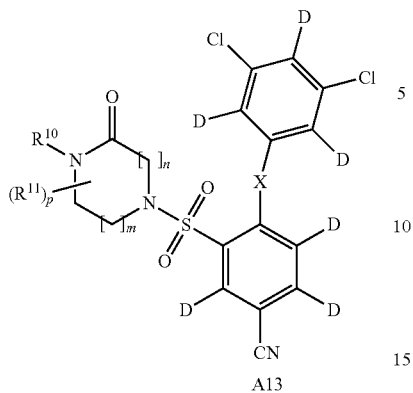

A13

Scheme III

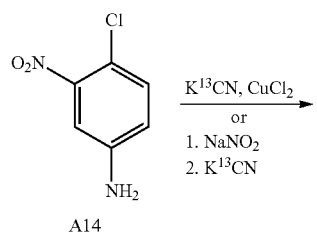

A14

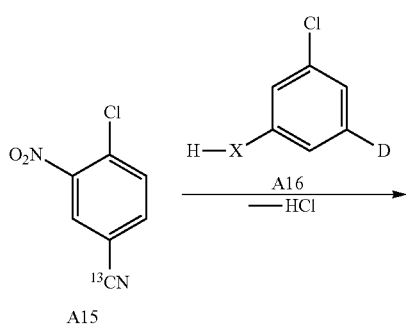

A15

A17

-continued

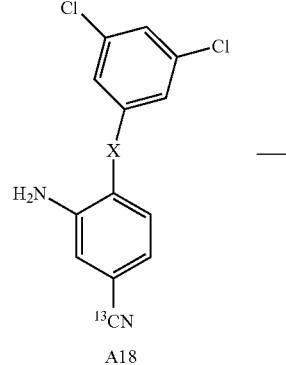

A18

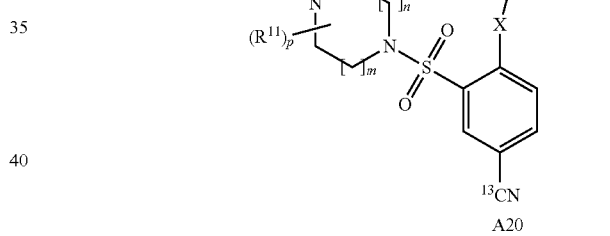

A19

A20

A compound provided herein may be administered alone, or in combination with one or more other compounds provided herein. The pharmaceutical compositions that comprise a compound provided herein, e.g., a compound of Formula I, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, Remington: The Science and Practice of Pharmacy, supra; Modified-Release Drug Delivery Technology, 2nd Edition, Rathbone et al., Eds., Marcel Dekker, Inc.: New York, N.Y., 2008).

In one embodiment, the pharmaceutical compositions are provided in a dosage form for oral administration, which comprise a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable excipients.

In another embodiment, the pharmaceutical compositions are provided in a dosage form for parenteral administration, which comprise a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable excipients.

In yet another embodiment, the pharmaceutical compositions are provided in a dosage form for topical administration, which comprise a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable excipients.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as *acacia*, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-3-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (*theobroma* oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as 1-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained- pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxyethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method of treating, preventing, or ameliorating one or more symptoms of a CCR3-mediated disease, disorder, or condition in a subject, which comprises administering to the subject a therapeutically effective amount of a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

In another embodiment, provided herein is a method of treating, preventing, or ameliorating one or more symptoms of a disease, disorder, or condition associated with CCR3 in a subject, which comprises administering to the subject a therapeutically effective amount of a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

In yet another embodiments, provided herein is a method of treating, preventing, or ameliorating one or more symptoms of a disease, disorder, or condition responsive to the modulation of CCR3 activity in a subject, comprising administering to the subject a therapeutically effective amount of a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

In yet another embodiment, provided herein is a method for treating, preventing, or ameliorating one or more symptoms of an eosinophil-related disease, disorder, or condition in a subject, comprising administering to the subject a therapeutically effective amount of a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

In yet another embodiment, provided herein is a method for treating, preventing, or ameliorating one or more symptoms of a basophil-related disease, disorder, or condition in a subject, comprising administering to a subject, a therapeutically effective amount of a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

In yet another embodiment, provided herein is a method for treating, preventing, or ameliorating one or more symptoms of a mast cell-related disease, disorder, or condition in a subject, comprising administering to a subject a therapeutically effective amount of a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

In still another embodiment, provided is a method for treating, preventing, or ameliorating one or more symptoms of an inflammatory disease in a subject, comprising administering to the subject a therapeutically effective amount of a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

In one embodiment, the subject is a mammal. In another embodiment, the subject is a human.

The diseases, disorders, or conditions treatable with a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof, include, but are not limited to, (1) inflammatory or allergic diseases, including systemic anaphylaxis and hypersensitivity disorders, atopic dermatitis, urticaria, drug allergies, insect sting allergies, food allergies (including celiac disease), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, and bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain embodiments, the disease, disorder, or condition is selected from the group consisting of asthma, allergic asthma, exercise induced asthma, allergic rhinitis, perennial allergic rhinitis, seasonal allergic rhinitis, atopic dermatitis, contact hypersensitivity, contact dermatitis, conjunctivitis, allergic conjunctivitis, eosinophilic bronchitis, food allergies, eosinophilic gastroenteritis, inflammatory bowel disease, ulcerative colitis, Crohn's disease, mastocytosis, hyper IgE syndrome, systemic lupus erythematous, psoriasis, acne, multiple sclerosis, allograft rejection, reperfusion injury, Churg-Strauss syndrome, sinusitis, basophilic leukemia, chronic urticaria, basophilic leukocytosis, eczema, COPD (chronic obstructive pulmonary disorder), arthritis, rheumatoid arthritis, psoriatic arthritis, and osteoarthritis.

In certain embodiments, the disease, disorder, or condition is asthma, exercise induced asthma, allergic rhinitis, atopic dermatitis, COPD, or allergic conjunctivitis.

Depending on the disease, disorder, or condition to be treated, and the subject's condition, the compounds or pharmaceutical compositions provided herein can be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration. Also provided is administration of the compounds or pharmaceutical compositions provided herein in a depot formulation, in which the active ingredient is released over a predefined time period.

In the treatment, prevention, or amelioration of one or more symptoms of asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, or other conditions, disorders or diseases associated with a CCR3 receptor, an appropriate dosage level generally is ranging from about 0.001 to 100 mg/kg/day, from about 0.01 to about 75 mg/kg/day, from about 0.1 to about 50 mg/kg/day, from about 0.5 to about 25 mg/kg/day, or from about 1 to about 20 mg/kg/day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg/day. In certain embodiments, the dosage level is ranging from about 0.001 to about 100 mg/kg/day. In certain embodiments, the dosage level is ranging from about 0.01 to about 75 mg/kg/day. In certain embodiments, the dosage level is ranging from about 0.1 to about 50 mg/kg/day. In certain embodiments, the dosage level is ranging from about 0.5 to about 25 mg/kg/day. In certain embodiments, the dosage level is ranging from about 1 to about 20 mg/kg/day.

For oral administration, the pharmaceutical compositions provided herein can be formulated in the form of tablets containing from about 1.0 to about 1,000 mg of the active ingredient, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The pharmaceutical compositions can be administered on a regimen of 1 to 4 times per day, including once, twice, three times, and four times per day.

It will be understood, however, that the specific dose level and frequency of dosage for any particular patient can be varied and will depend upon a variety of factors, including the activity of the specific compound employed, the metabolic stability and length of action of that compound, the age, body weight, general health, sex, diet, mode and time of administration, rate of excretion, drug combination, the severity of the particular condition, and the host undergoing therapy.

In one embodiment, provided herein is a method of modulating CCR3 activity, comprising contacting a CCR3 receptor with a compound provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the CCR3 receptor is expressed by a cell.

The compounds provided herein, e.g., a compound of Formula I, or an enantiomer, a mixture of enantiomers, a mixture of two or more diastereomers, a tautomer, or a mixture of two or more tautomers thereof; or a pharmaceutically acceptable salt, solvate, hydrate, or prodrug thereof, can also be combined or used in combination with other agents useful in the treatment, prevention, or amelioration of one or more symptoms of the disorders, diseases, or conditions for which the compounds provided herein are useful, including asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, infectious diseases, and those pathologies noted above.

In certain embodiments, a compound provided herein can be combined with one or more steroidal drugs known in the art, including, but not limited to, aldosterone, beclometasone, betamethasone, deoxycorticosterone acetate, fludrocortisone, hydrocortisone (cortisol), prednisolone, prednisone, methylprednisolone, dexamethasone, and triamcinolone.

In certain embodiments, a compound provided herein can be combined with one or more antibacterial agents known in the art, including, but not limited to, amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristin, demeclocycline, dicloxacillin, dirithromycin, doxycycline, erythromycin, enrofloxacin, ertepenem, ethambutol, flucloxacillin, fosfomycin, furazolidone, gatifloxacin, geldanamycin, gentamicin, herbimycin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, neomycin, netilmicin, nitrofurantoin, norfloxacin, ofloxacin, oxytetracycline, penicillin, piperacillin, platensimycin, polymyxin B, prontocil, pyrazinamide, quinupristine, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, a compound provided herein can be combined with one or more antifungal agents known in the art, including, but not limited to, amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole.

In certain embodiments, a compound provided herein can be combined with one or more anticoagulants known in the art, including, but not limited to, acenocoumarol, argatroban, bivalirudin, lepirudin, fondaparinux, heparin, phenindione, warfarin, and ximelagatran.

In certain embodiments, a compound provided herein can be combined with one or more thrombolytics known in the art, including, but not limited to, anistreplase, reteplase, t-PA (alteplase activase), streptokinase, tenecteplase, and urokinase.

In certain embodiments, a compound provided herein can be combined with one or more non-steroidal anti-inflammatory agents known in the art, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin.

In certain embodiments, a compound provided herein can be combined with one or more antiplatelet agents known in the art, including, but not limited to, abciximab, cilostazol, clopidogrel, dipyridamole, ticlopidine, and tirofibin.

A compound provided herein can also be administered in combination with other classes of compounds, including, but not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) famesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as *vinca* alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

Such other agents, or drugs, can be administered, by a route and in an amount commonly used therefor, simultaneously or sequentially with a compound provided herein, e.g., a compound of Formula I, or a single enantiomer, a mixture of enantiomers, or a mixture of diastereomers thereof; or a pharmaceutically acceptable salt, solvate, or prodrug thereof. When a compound provided herein is used contemporaneously with one or more other drugs, a pharmaceutical composition containing such other drugs in addition to the compound provided herein can be utilized, but is not required. Accordingly, the pharmaceutical compositions provided herein include those that also contain one or more other active ingredients or therapeutic agents, in addition to a compound provided herein.

The weight ratio of a compound provided herein to the second active ingredient can be varied, and will depend upon the effective dose of each ingredient. Generally, an effective dose of each will be used. Thus, for example, when a compound provided herein is combined with a NSAID, the weight ratio of the compound to the NSAID can range from about 1,000:1 to about 1:1,000, or about 200:1 to about 1:200. Combinations of a compound provided herein and other active ingredients will generally also be within the aforementioned range, but in each case, an effective dose of each active ingredient should be used.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by a medical practitioner, can simplify the administration of appropriate amounts of active ingredients to a subject. In certain embodiments, the kit provided herein includes a container and a dosage form of a compound provided herein, e.g., a compound of Formula I, or a single enantiomer, a mixture of enantiomers, or a mixture of diastereomers thereof; or a pharmaceutically acceptable salt, solvate, or prodrug thereof.

In certain embodiments, the kit includes a container comprising a dosage form of a compound provided herein, e.g., a compound of Formula I, or a single enantiomer, a mixture of enantiomers, or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredient(s). Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); HPLC (high pressure liquid chromatography); THF (tetrahydrofuran); and DMSO-$d_6$ (deuterated dimethylsulfoxide).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify applicable chemistry through the use of specific examples and are not indicative of the scope of the disclosure.

Example 1

Preparation of 4-(3,5-dichloro-2,4,6-trideuterium-phenoxy)-3-(3-oxo-piperazine-1-sulfonyl)-2,5,6-trideuteriumbenzonitrile 36

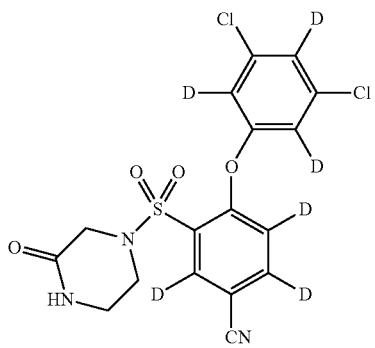

4-(3,5-Dichloro-2,4,6-trideuteriumphenoxy)-3-(3-oxo-piperazine-1-sulfonyl)-2,5,6-trideuteriumbenzonitrile 36 was synthesized as shown in Scheme 1.

Preparation of 4-chloro-2,3,6-trideuterium-5-nitrobenzonitrile B2. To a solution of 4-chlorobenzonitrile-$d_4$ B1 (2.00 g, 14.13 mmol) in fuming nitric acid (26 mL) in an ice bath was added dropwise sulfuric acid (20 mL) over 90 min. After stirred for additional 2 hrs, the reaction mixture was poured into ice water (500 mL). The resulting white precipitate was collected by filtration and dried to yield 4-chloro-2,3,6-trideuterium-5-nitrobenzonitrile B2 as a white solid (2.27 g, 100% purity, 86.9% yield).

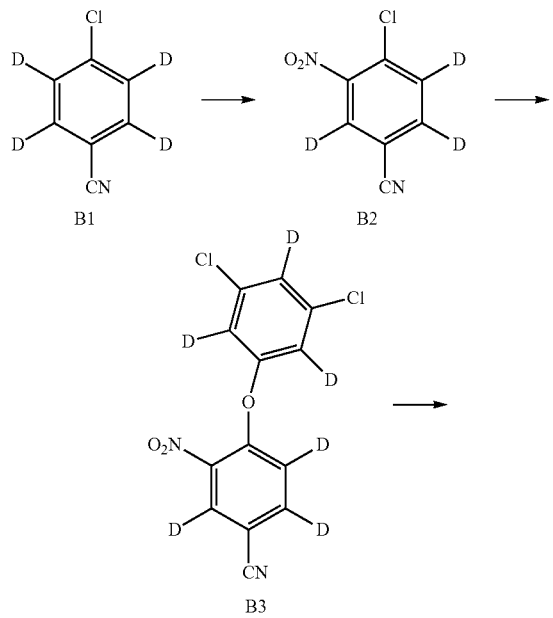

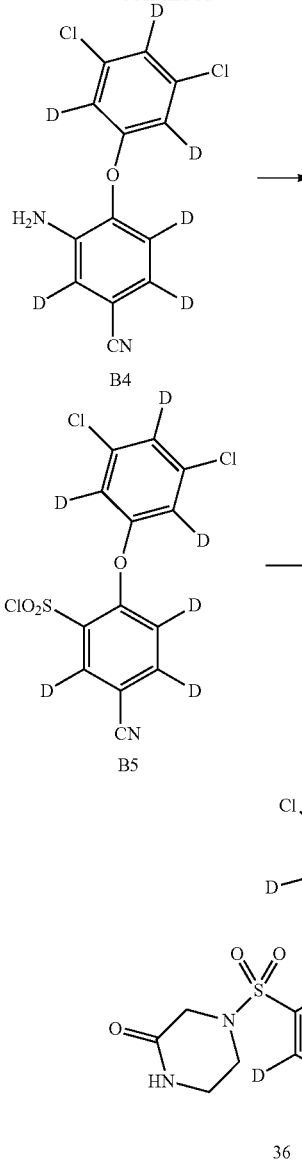

Preparation of 4-(3,5-dichloro-2,4,6-trideuteriumphenoxy)-2,5,6-trideuterium-3-nitrobenzonitrile B3. To a solution of 4-chloro-2,3,6-trideuterium-5-nitrobenzonitrile B2 (92.2 mg, 0.56 mmol) in THF (4 mL) were added potassium carbonate (232 mg) and 3,5-dichloro-2,4,6-trideuteriumphenol (104 mg, 0.56 mmol). The reaction mixture was refluxed at 70° C. overnight. The reaction mixture was diluted with EtOAc and filtered. The EtOAc solution was concentrated and then treated with hexanes. The resulting solid was filtered and dried to yield 4-(3,5-dichloro-2,4,6-trideuteriumphenoxy)-2,5,6-trideuterium-3-nitrobenzonitrile B3 as a yellow powder (147 mg, 100% purity, 83.3% yield).

Preparation of 3,5-dichloro-2,4,6-trideuteriumphenoxy)-3-amino-2,5,6-trideuteriumbenzonitrile B4. To a solution of tin(II) chloride (216 mg, 1.14 mmol) in conc. HCl (38 μL) and ethanol (10 mL) was added 4-(3,5-dichloro-2,4,6-trideuteriumphenoxy)-2,5,6-trideuterium-3-nitrobenzonitrile B3 (120 mg, 0.38 mmol) slowly at 70° C. The reaction mixture was refluxed overnight and then poured into ice water. The resulting precipitate was collected by filtration to yield 3,5-dichloro-2,4,6-trideuteriumphenoxy)-3-amino-2,5,6-trideuteriumbenzonitrile B4 (98 mg, 85.2% purity, 90.5% yield).

Preparation of 2-(3,5-dichloro-2,4,6-trideuteriumphenoxy)-3,4,6-trideuterium-5-cyanobenzene-1-sulfonyl chloride B5. A saturated $SO_2$ solution in glacial acid was prepared by bubbling $SO_2$ into glacial acetic acid (2 mL) until no further change in mass was observed (about 0.5 hrs). A reaction mixture was prepared by grounding 3,5-dichloro-2,4,6-trideuteriumphenoxy)-3-amino-2,5,6-trideuteriumbenzonitrile B4 (98 mg, 0.34 mmol) into fine powder and adding the grounded compound in one portion to a mixture of conc. aqueous HCl (0.5 mL) and glacial acetic acid (0.5 mL). After white precipitates appeared, the reaction mixture was cooled to at least −10° C. in a dry-ice-ethanol bath while stirring. Sodium nitrite (26 mg, 0.37 mmol) dissolved in minimal water was added dropwise to the reaction mixture, such that the temperature did not exceed −5° C. After all the sodium nitrile was added, the mixture was stirred at a temperature below −5° C. for 30 min. In the meantime, copper (I) chloride (3 mg, 0.03 mmol) and copper (II) chloride dihydrate (15 mg, 0.09 mmol) were added to the saturated $SO_2$ solution and the resulting solution was stirred for 15 min. The saturated $SO_2$ solution was then cooled to 10 OC in an ice bath. The diazonium in the reaction mixture was added in portions to the saturated $SO_2$ solution, such that the temperature did not exceed 30° C. After all the diazonium was added, the solution was stirred for 30 min, or until gas evolution ceased, forming a green solution. The solution was poured into 100 mL of ice water with stirring over the course of 5 min. The mixture was filtered, washed with copious water, and tried overnight in vacuum to yield 2-(3,5-dichloro-2,4,6-trideuteriumphenoxy)-3,4,6-trideuterium-5-cyanobenzene-1-sulfonyl chloride B5 as a yellow powder (91 mg, 90% purity, 73% yield).

Preparation of 4-(3,5-dichloro-2,4,6-trideuteriumphenoxy)-3-(3-oxo-piperazine-1-sulfonyl)-2,5,6-trideuteriumbenzonitrile 36. To a solution of 2-(3,5-dichloro-2,4,6-trideuteriumphenoxy)-3,4,6-trideuterium-5-cyanobenzene-1-sulfonyl chloride B5 (90.6 mg, 0.25 mmol) in THF (4 mL) was added 2-oxopiperazine (25 mg, 0.25 mmol). After the mixture was sonicated, triethylamine (25 mg, 0.25 mmol) was then added and the reaction mixture was stirred at room temperature until completion as determined by HPLC. The reaction mixture was filtered and concentrated. The resulting residue was redissolved in THF. The mixture was heated in 30% $MeOH/H_2O$ to form a slurry, which was filtered to yield 4-(3,5-dichloro-2,4,6-trideuteriumphenoxy)-3-(3-oxo-piperazine-1-sulfonyl)-2,5,6-trideuteriumbenzonitrile 36 as an off-white solid (72 mg, 97.8% purity, 67% yield). Melting point: 207-210° C. $^1$H NMR (500 MHz, DMSO-$D_6$) δ 9.54 (br, 1H), 3.81 (s, 2H), 3.52 (t, J1=J2=6 Hz, 2H), 3.11 (m, 2H).

Example 2

Pharmacokinetic Studies

Pharmacokinetic properties of 4-(3,5-dichloro-2,4,6-trideuteriumphenoxy)-3-(3-oxo-piperazine-1-sulfonyl)-2,5,6-trideuteriumbenzonitrile 36 and 4-(3,5-dichlorophenoxy)-3-(3-oxo-piperazine-1-sulfonyl)benzonitrile C1 were determined using rats. Animals were randomized into two groups, each having 3 rats. 4-(3,5-Dichloro-2,4,6-trideuteriumphenoxy)-3-(3-oxo-piperazine-1-sulfonyl)-2,5,6-trideuteriumbenzonitrile 36 and 4-(3,5-dichlorophenoxy)-3-(3-oxo-piperazine-1-sulfonyl)benzonitrile C1 were administered at 3 mg/kg in $EtOH/Solutol/H_2O$ formulations. Pharmacokinetic parameters of 4-(3,5-dichloro-2,4,6-trideuteriumphenoxy)-3-(3-oxo-piperazine-1-sulfonyl)-2,5,6-trideuteriumbenzonitrile 36 and 4-(3,5-dichlorophenoxy)-3-(3-oxo-piperazine-1-sulfonyl)benzonitrile C1 are summarized in Table 2. 4-(3,5-dichlorophenoxy)-3-(3-oxo-piperazine-1-sulfonyl)benzonitrile C1 was synthesized according to the procedure as described in U.S. Pat. App. Pub. No.: US 2011/0218207, the disclosure of which is incorporated herein by reference in its entirety.

TABLE 2

| Cmpd # | Compound C1 | | | Compound 36 | | |
|---|---|---|---|---|---|---|
| | Rat 1 | Rat 2 | Rat 3 | Rat 1 | Rat 2 | Rat 3 |
| $C_{max}$ (ng/mL) | 34.4 | 65.8 | 59.9 | 166.0 | 46.3 | 128.0 |
| $T_{max}$ (hr) | 2.0 | 4.0 | 2.0 | 2.0 | 4.0 | 0.3 |
| Half-life (hr) | 5.517 | 3.720 | 4.045 | 3.296 | 1.122 | 1.515 |
| AUC (μg · hr/L) | 199.7 | 449.8 | 317.4 | 819.8 | 271.7 | 489.8 |
| $AUC_{norm}$ (μg · hr/L) | 66.6 | 149.9 | 105.8 | 273.3 | 90.6 | 163.3 |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. An isotopically enriched compound of Formula II:

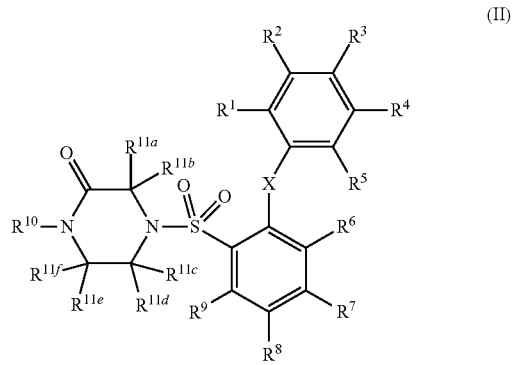

or an enantiomer, a mixture of enantiomers, a mixture of two or more diastereomers, a tautomer, or a mixture of two or more tautomers thereof; or a pharmaceutically acceptable salt thereof;

wherein:
$R^1$, $R^2$, $R^3$, $R^4$, and $R^5$, are each independently hydrogen, deuterium, halo, or $C_{1-6}$ alkyl;
$R^6$, $R^7$, and $R^9$ are each independently hydrogen or deuterium;
$R^8$ is cyano or nitro;
$R^{10}$ is (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)OR$^{1a}$, —C(O)NR$^{1b}$R$^{1c}$, —C(NR$^{1a}$)NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{11a}$, R$^{11b}$, R$^{11c}$, R$^{11d}$, R$^{11e}$, and R$^{11f}$ are each independently hydrogen or deuterium;

X is O or S;

wherein each alkyl, alkenyl, alkynyl, cycloalkyl, aryl, aralkyl, heterocyclyl, and heteroaryl is optionally substituted with one or more substituents Q, where each Q is independently selected from (a) deuterium, cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each of which is further optionally substituted with one or more substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more substituents Q$^a$; or (iii) each pair of R$^b$ and R$^c$ together with the N atom to which they are attached form heterocyclyl, optionally substituted with one or more substituents Q$^a$;

wherein each Q$^a$ is independently selected from the group consisting of (a) deuterium, cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) each pair of R$^f$ and R$^g$ together with the N atom to which they are attached form heterocyclyl.

2. The compound of claim 1, wherein R$^{11a}$ and R$^{11b}$ are hydrogen.

3. The compound of claim 1, wherein R$^{11a}$ and R$^{11b}$ are deuterium.

4. The compound of claim 1, wherein R$^{11c}$ and R$^{11d}$ are hydrogen.

5. The compound of claim 1, wherein R$^{11c}$ and R$^{11d}$ are deuterium.

6. The compound of claim 1, wherein R$^{11e}$ and R$^{11f}$ are hydrogen.

7. The compound of claim 1, wherein R$^{11e}$ and R$^{11f}$ are deuterium.

8. The compound of claim 1, wherein two of R$^1$, R$^2$, R$^3$, R$^4$, and R$^5$ are halo or C$_{1-6}$ alkyl, optionally substituted with one or more substituents Q; and the remaining three are hydrogen or deuterium.

9. The compound of claim 8, wherein two of R$^1$, R$^2$, R$^3$, R$^4$, and R$^5$ are chloro, methyl, —CH$_2$D, —CHD$_2$, or -CD$_3$; and the remaining three are hydrogen or deuterium.

10. The compound of claim 1, wherein R$^1$ is hydrogen.

11. The compound of claim 1, wherein R$^1$ is deuterium.

12. The compound of claim 1, wherein R$^2$ is chloro.

13. The compound of claim 1, wherein R$^2$ is methyl, —CH$_2$D, —CHD$_2$, or -CD$_3$.

14. The compound of claim 1, wherein R$^1$ is chloro.

15. The compound of claim 1, wherein R$^1$ is methyl, —CH$_2$D, —CHD$_2$, or -CD$_3$.

16. The compound of claim 1, wherein R$^2$ is hydrogen.

17. The compound of claim 1, wherein R$^2$ is deuterium.

18. The compound of claim 1, wherein R$^4$ is chloro.

19. The compound of claim 1, wherein R$^4$ is methyl, —CH$_2$D, —CHD$_2$, or -CD$_3$.

20. The compound of claim 1, wherein R$^3$ is hydrogen.

21. The compound of claim 1, wherein R$^3$ is deuterium.

22. The compound of claim 1, wherein R$^5$ is hydrogen.

23. The compound of claim 1, wherein R$^5$ is deuterium.

24. The compound of claim 1, wherein R$^6$ is hydrogen.

25. The compound of claim 1, wherein R$^6$ is deuterium.

26. The compound of claim 1, wherein R$^7$ is hydrogen.

27. The compound of claim 1, wherein R$^7$ is deuterium.

28. The compound of claim 1, wherein R$^9$ hydrogen.

29. The compound of claim 1, wherein R$^9$ is deuterium.

30. The compound of claim 1, wherein R$^8$ is cyano.

31. The compound of claim 1, wherein R$^8$ is —$^{13}$CN.

32. The compound of claim 1, wherein R$^8$ is nitro.

33. The compound of claim 1, wherein R$^{10}$ is hydrogen.

34. The compound of claim 1, wherein R$^{10}$ is deuterium.

35. The compound of claim 1, wherein X is O.

36. The compound of claim 1, wherein X is S.

37. The compound of claim 1 selected from the group consisting of:

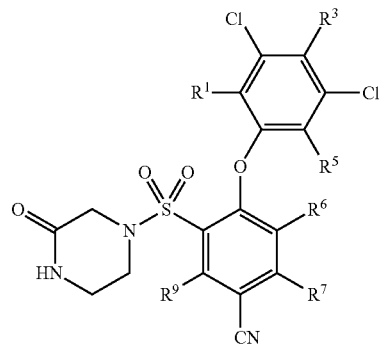

| Cmpd. | R$^1$ | R$^3$ | R$^5$ | R$^6$ | R$^7$ | R$^9$ |
|---|---|---|---|---|---|---|
| 1 | D | H | H | H | H | H |
| 2 | H | D | H | H | H | H |
| 3 | H | H | D | H | H | H |

-continued

| Cmpd. | R¹ | R³ | R⁵ | R⁶ | R⁷ | R⁹ |
|---|---|---|---|---|---|---|
| 4 | H | H | H | D | H | H |
| 5 | H | H | H | H | D | H |
| 6 | H | H | H | H | H | D |
| 7 | D | D | H | H | H | H |
| 8 | D | H | D | H | H | H |
| 9 | D | H | H | D | H | H |
| 10 | D | H | H | H | D | H |
| 11 | D | H | H | H | H | D |
| 12 | H | D | D | H | H | H |
| 13 | H | D | H | D | H | H |
| 14 | H | D | H | H | D | H |
| 15 | H | D | H | H | H | D |
| 16 | H | H | D | D | H | H |
| 17 | H | H | D | H | D | H |
| 18 | H | H | D | H | H | H |
| 19 | H | H | H | D | D | H |
| 20 | H | H | H | D | H | D |
| 21 | H | H | H | H | D | D |
| 22 | D | D | D | H | H | H |

-continued

| Cmpd. | R¹ | R³ | R⁵ | R⁶ | R⁷ | R⁹ |
|---|---|---|---|---|---|---|
| 23 | D | D | D | D | H | H |
| 24 | D | D | D | H | D | H |
| 25 | D | D | D | H | H | D |
| 26 | D | D | D | D | D | H |
| 27 | D | D | D | D | H | D |
| 28 | D | D | D | D | H | D |
| 29 | H | H | H | D | D | D |
| 30 | D | H | H | D | D | D |
| 31 | H | D | H | D | D | D |
| 32 | H | H | D | D | D | D |
| 33 | D | D | H | D | D | D |
| 34 | D | H | D | D | D | D |
| 35 | H | D | D | D | D | D |
| 36 | D | D | D | D | D | D | and pharmaceutically acceptable salts thereof.

38. The compound of claim 1 selected from the group consisting of:

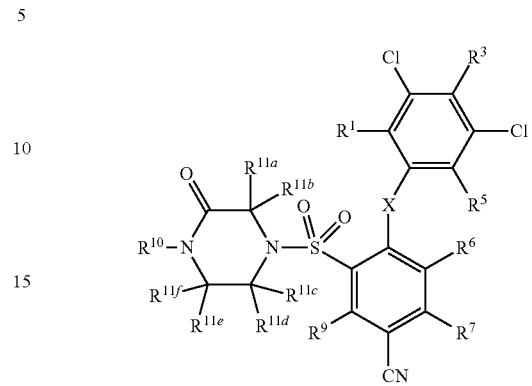

| Cmpd. | R¹ | R³ | R⁵ | R⁶ | R⁷ | R⁹ | R¹¹ᵃ | R¹¹ᵇ | R¹¹ᶜ | R¹¹ᵈ | R¹¹ᵉ | R¹¹ᶠ |
|---|---|---|---|---|---|---|---|---|---|---|---|---|
| 51 | H | H | H | H | H | H | D | D | H | H | H | H |
| 52 | H | H | H | H | H | H | H | H | D | D | H | H |
| 53 | H | H | H | H | H | H | H | H | H | H | D | D |
| 54 | H | H | H | H | H | H | D | D | D | D | H | H |
| 55 | H | H | H | H | H | H | D | D | H | H | D | D |
| 56 | H | H | H | H | H | H | H | H | D | D | D | D |
| 57 | H | H | H | H | H | H | D | D | D | D | D | D |
| 58 | D | D | D | H | H | H | D | D | H | H | H | H |
| 59 | D | D | D | H | H | H | H | H | D | D | H | H |
| 60 | D | D | D | H | H | H | H | H | H | H | D | D |
| 61 | D | D | D | H | H | H | D | D | D | D | H | H |
| 62 | D | D | D | H | H | H | D | D | H | H | D | D |
| 63 | D | D | D | H | H | H | H | H | D | D | D | D |
| 64 | D | D | D | H | H | H | D | D | D | D | D | D |
| 65 | H | H | H | D | D | D | D | D | H | H | H | H |
| 66 | H | H | H | D | D | D | H | H | D | D | H | H |
| 67 | H | H | H | D | D | D | H | H | H | H | D | D |
| 68 | H | H | H | D | D | D | D | D | D | D | H | H |
| 69 | H | H | H | D | D | D | D | D | H | H | D | D |
| 70 | H | H | H | D | D | D | H | H | D | D | D | D |
| 71 | H | H | H | D | D | D | D | D | D | D | D | D |
| 72 | D | D | D | D | D | D | D | D | H | H | H | H |
| 73 | D | D | D | D | D | D | H | H | D | D | H | H |
| 74 | D | D | D | D | D | D | H | H | H | H | D | D |
| 75 | D | D | D | D | D | D | D | D | D | D | H | H |
| 76 | D | D | D | D | D | D | D | D | H | H | D | D |
| 77 | D | D | D | D | D | D | H | H | D | D | D | D |
| 78 | D | D | D | D | D | D | D | D | D | D | D | D | and pharmaceutically acceptable salts thereof.

39. The compound of claim 1, wherein the compound is deuterium enriched.

40. The compound of claim 1, wherein the compound is carbon-13 enriched.

41. The compound of claim 1, wherein at least one of the atoms as specified as isotopically enriched has isotopic enrichment of no less than about 5%.

42. The compound of claim 1, wherein the compound is a hydrochloride salt.

43. A pharmaceutical composition comprising a compound of claim 1, or an enantiomer, a mixture of enantiomers, a mixture of two or more diastereomers, a tautomer, or a mixture of two or more tautomers thereof; or a pharmaceutically acceptable salt thereof; and one or more pharmaceutically acceptable excipients.

44. The pharmaceutical composition of claim 43, further comprising a second therapeutic agent.

45. The pharmaceutical composition of claim 44, wherein the pharmaceutical composition is formulated for single dose administration.

46. The pharmaceutical composition of claim 45, wherein the pharmaceutical composition is formulated for single dose administration.

47. The pharmaceutical composition of claim 46, wherein the oral dosage form is a tablet or capsule.

* * * * *